(12) United States Patent
Katagiri et al.

(10) Patent No.: US 9,949,369 B2
(45) Date of Patent: Apr. 17, 2018

(54) CYANATE ESTER COMPOUND, CURABLE RESIN COMPOSITION CONTAINING THE SAME, AND HARDENED PRODUCT THEREOF

(71) Applicant: MITSUBISHI GAS CHEMICAL COMPANY, INC., Tokyo (JP)

(72) Inventors: Masayuki Katagiri, Niigata (JP); Keita Tokuzumi, Niigata (JP); Makoto Tsubuku, Tokyo (JP); Tomoo Tsujimoto, Niigata (JP); Kenji Arii, Tokyo (JP); Takashi Kobayashi, Tokyo (JP); Masanobu Sogame, Tokyo (JP); Yoshinori Mabuchi, Tokyo (JP); Sotaro Hiramatsu, Tokyo (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 49 days.

(21) Appl. No.: 15/023,876

(22) PCT Filed: Oct. 24, 2014

(86) PCT No.: PCT/JP2014/078304
§ 371 (c)(1),
(2) Date: Mar. 22, 2016

(87) PCT Pub. No.: WO2015/060418
PCT Pub. Date: Apr. 30, 2015

(65) Prior Publication Data
US 2016/0262263 A1 Sep. 8, 2016

(30) Foreign Application Priority Data

Oct. 25, 2013 (JP) ................................. 2013-222021
Jan. 23, 2014 (JP) ................................. 2014-010135

(51) Int. Cl.
C07C 261/02 (2006.01)
H05K 1/05 (2006.01)
(Continued)

(52) U.S. Cl.
CPC ......... *H05K 1/0346* (2013.01); *C07C 261/02* (2013.01); *C07C 265/14* (2013.01);
(Continued)

(58) Field of Classification Search
None
See application file for complete search history.

(56) References Cited

U.S. PATENT DOCUMENTS

| 4,748,270 A | 5/1988 | Murray et al. |
| 4,931,545 A | 6/1990 | Shimp et al. |

(Continued)

FOREIGN PATENT DOCUMENTS

| CN | 102026963 | 4/2011 |
| CN | 103180366 | 6/2013 |

(Continued)

OTHER PUBLICATIONS

Search Report issued in Patent Application No. PCT/JP2014/078304, dated Apr. 30, 2015.
(Continued)

*Primary Examiner* — Vu A Nguyen
(74) *Attorney, Agent, or Firm* — Greenblum & Bernstein, P.L.C.

(57) ABSTRACT

The present invention is a cyanate ester compound represented by the following formula (1):
(Continued)

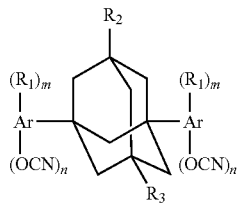

wherein Ar represents an aromatic ring; $R_1$ each independently represents a hydrogen atom, an alkyl group, or an aryl group; n each independently represents an integer of 1 to 3; m+n is the same as the total number of hydrogen atoms in a monovalent aromatic group containing the aromatic ring and the hydrogen atoms; $R_2$ represents a hydrogen atom (excluding a case where Ar represents a benzene ring; n each represents 1; $R_1$ represents a hydrogen atom; m each represents 4, and a cyanate group is bonded to the benzene ring in the 4-position relative to an adamantyl group), or an alkyl group having 1 to 4 carbon atoms; and $R_3$ represents a hydrogen atom or an alkyl group having 1 to 4 carbon atoms.

23 Claims, 9 Drawing Sheets

(51) Int. Cl.

| | |
|---|---|
| H05K 1/03 | (2006.01) |
| C08G 73/06 | (2006.01) |
| C08L 79/04 | (2006.01) |
| C07C 265/14 | (2006.01) |
| C08G 18/02 | (2006.01) |
| C08K 3/00 | (2018.01) |
| C08L 61/04 | (2006.01) |
| C08L 63/00 | (2006.01) |
| C08L 79/00 | (2006.01) |
| C09J 179/00 | (2006.01) |

(52) U.S. Cl.
CPC ......... *C08G 18/02* (2013.01); *C08G 73/0655* (2013.01); *C08K 3/0008* (2013.01); *C08L 61/04* (2013.01); *C08L 63/00* (2013.01); *C08L 79/00* (2013.01); *C08L 79/04* (2013.01); *C09J 179/00* (2013.01); *C07C 2603/74* (2017.05)

(56) References Cited

U.S. PATENT DOCUMENTS

| 9,475,761 B2 * | 10/2016 | Katagiri ............... C07C 261/02 |
| 2009/0130488 A1 | 5/2009 | Sugano et al. |
| 2011/0009559 A1 | 1/2011 | Mullins et al. |
| 2011/0009562 A1 * | 1/2011 | Mullins ............... C07C 37/20 |
| | | 524/595 |
| 2013/0281640 A1 | 10/2013 | Tsubuku et al. |
| 2015/0299110 A1 | 10/2015 | Katagiri et al. |

FOREIGN PATENT DOCUMENTS

| EP | 2 913 302 | 9/2015 |
| JP | 61-500120 | 1/1986 |
| JP | 6-271669 | 9/1994 |
| JP | 11-124433 | 5/1999 |
| JP | 3081996 | 6/2000 |
| JP | 2000-191776 | 7/2000 |
| JP | 4407823 | 2/2010 |
| JP | 2010-180147 | 8/2010 |
| JP | 4654770 | 3/2011 |
| JP | 2011-132167 | 7/2011 |
| JP | 2012-36114 | 2/2012 |
| JP | 5104312 | 12/2012 |
| TW | 200946485 | 11/2009 |
| TW | 201237016 | 9/2012 |
| WO | 85-02185 | 5/1985 |
| WO | 2012/057144 | 5/2012 |
| WO | 2014/065422 | 5/2014 |

OTHER PUBLICATIONS

International Preliminary Report on Patentability issued in Patent Application No. PCT/JP2014/078304, dated Apr. 26, 2016.

* cited by examiner

CYANATE ESTER COMPOUND, CURABLE RESIN COMPOSITION CONTAINING THE SAME, AND HARDENED PRODUCT THEREOF

TECHNICAL FIELD

The present invention relates to a cyanate ester compound, a curable resin composition containing the compound, a hardened product thereof, and a prepreg for structural materials, a sealing material, a fiber-reinforced composite material, and an adhesive which contain the curable resin composition.

BACKGROUND ART

Cyanate ester compounds produce triazine rings by curing and have high heat resistance and excellent electrical properties and therefore are widely used as raw materials of various functional polymer materials such as structural composite materials, adhesives, electrical insulating materials, and electrical and electronic components. However, in recent years, with an advance in required performance in these application fields, various properties required as functional polymer materials have become increasingly strict. Examples of such properties include flame retardancy, heat resistance, a low coefficiency of thermal expansion, low water-absorbing property, a low dielectric constant, a low dielectric loss tangent, weather resistance, chemical resistance, and high fracture toughness. However, functional polymer materials have not always satisfied these required properties so far.

For example, a problem in the semiconductor package material field is that with the thinning of base materials, warpage occurs due to the mismatch of the coefficiencies of thermal expansion between a semiconductor chip and a base material. As means for solving this, it is required to improve the low thermal expansion and high heat resistance of the functional polymer material itself used for the base material. In addition, from the viewpoint of consideration on human bodies and environment, the use of lead-free solder has been promoted for the soldering of a printed wiring board. Also, from the viewpoint of resistance to a reflow step at a high temperature attended with the lead-free soldering, it has been desired to improve low coefficiency of thermal expansion and high heat resistance for a functional polymer material.

From the viewpoint of improving the flame retardancy of a functional polymer material, the functional polymer material conventionally contain halogen atoms or phosphorus atoms in some cases. However, the halogen atoms are likely to generate halogen gas having a risk of causing environmental pollution during combustion and are also likely to reduce the insulating properties of a final product. The phosphorus atoms often decline required properties other than flame retardancy (heat resistance, moisture resistance, and low water-absorbing property or the like). Hence, it has also been desired to improve the flame retardancy of the functional polymer material without containing halogen atoms or phosphorus atoms.

Furthermore, when a laminate for printed wiring board applications or the like is produced, a prepreg is made by first dissolving an pre-hardened monomer which is a precursor of a functional polymer material in a solvent, such as methyl ethyl ketone, to prepare a varnish, then impregnating a glass cloth with the varnish, and drying it. Therefore, it has also been required to improve the solvent solubility of the monomer.

As an example in which a hardened product of a single cyanate ester compound having low thermal expansion and heat resistance is obtained, the use of a bifunctional cyanatophenyl-based cyanate ester compound in which the hydrogen of a methylene group bonding cyanatophenyl groups to each other is replaced by a particular alkyl group (1,1-bis (4-cyanatophenyl)isobutane), has been proposed (see Patent Document 1). As an example in which a hardened product of a single cyanate ester compound having low thermal expansion and flame retardancy is obtained, the use of a cyanate ester compound having an aralkyl structure has been proposed (for example, see Patent Document 2). Furthermore, as examples for providing a hardened product of a simple cyanate ester compound having flame retardancy and heat resistance, the uses of a cyanate ester compound containing an isocyanuric acid skeleton (see Patent Document 3), a cyanate ester compound containing a triazine skeleton (see Patent Document 4), and a bifunctional cyanatophenyl-based cyanate ester compound, in which the hydrogen in a methylene group bonding cyanatophenyl groups is replaced by a biphenyl group (see Patent Document 5), and the combination of a bisphenol A-based cyanate ester compound with a cyanate ester compound containing an imide skeleton (see Patent Document 6) have been proposed.

In recent years, high integration and/or miniaturization of semiconductors that are widely used for electronic devices, communication devices, and personal computers or the like have been increasingly accelerated. With such high integration and/or miniaturization, various properties required for laminates for semiconductor packaging, which are used for printed wiring boards, have become increasingly strict. Examples of the required properties include low water-absorbing property, heat resistance after moisture absorption, flame retardancy, a low dielectric constant, a low dielectric loss tangent, a low coefficiency of thermal expansion, heat resistance, and chemical resistance. However, these required properties have not been necessarily satisfied.

Conventionally, a cyanate ester compound has been known as a resin for printed wiring boards having excellent heat resistance and electrical properties. For example, a resin composition containing a bisphenol A-based cyanate ester compound and another thermosetting resin or the like has been widely used as a material for printed wiring boards or the like. The bisphenol A-based cyanate ester compound has excellent properties such as electrical properties, mechanical properties, and chemical resistance or the like. However, in some cases, this cyanate ester compound is insufficient in terms of low water-absorbing property, heat resistance after moisture absorption, and flame retardancy. Hence, for the purpose of further improving such properties, studies regarding various cyanate ester compounds having different structures have been conducted.

As a resin having a structure which is different from that of the bisphenol A-based cyanate ester compound, a novolac-based cyanate ester compound has been frequently used (see Patent Document 7). However, the novolac-based cyanate ester compound is problematic in that it easily causes insufficient hardness, and in that the obtained hardened product has a high water absorption rate and decreased heat resistance after moisture absorption. Hence, prepolymerization of a novolac-based cyanate ester compound and a bisphenol A-based cyanate ester compound has been proposed as a method for solving these problems (see Patent Document 8).

As a method of improving flame retardancy, it has been proposed to use a fluorinated cyanate ester compound, or to mix a cyanate ester compound with a halogen-based compound or prepolymerize these compounds so as to allow a resin composition to contain the halogen-based compound (see Patent Documents 9 and 10).

CITATION LIST

Patent Document

Patent Document 1: National Publication of International Patent Application No. 2012/057144
Patent Document 2: Japanese Patent Publication No. 4407823
Patent Document 3: Japanese Patent Publication No. 4654770
Patent Document 4: Japanese Patent Application Laid-Open No. 2012-036114
Patent Document 5: Japanese Patent Publication No. 5104312
Patent Document 6: Japanese Patent Application Laid-Open No. 2010-180147
Patent Document 7: Japanese Patent Application Laid-Open No. 11-124433
Patent Document 8: Japanese Patent Application Laid-Open No. 2000-191776
Patent Document 9: Japanese Patent Publication No. 3081996
Patent Document 10: Japanese Patent Application Laid-Open No. 6-271669

SUMMARY OF INVENTION

Technical Problem

However, the present inventors have studied the above conventional techniques and, as a result, found that the flame retardancy (low degradability at a high temperature) of the bifunctional cyanatophenyl-based cyanate ester compound disclosed in Patent Document 1 is declined, when the hydrogen atom of a methylene group bonding cyanatophenyl groups to each other is replaced by an alkyl group. There is no description regarding flame retardancy at all in Patent Document 1. The cyanate ester compound having an aralkyl structure disclosed in Patent Document 2 was found to be poorly soluble in a solvent and difficult to be handled. Furthermore, there is no description or suggestion regarding a coefficiency of thermal expansion and/or solvent solubility at all in any of Patent Documents 3 to 6.

After all, so far, even if a simple cyanate ester compound having solvent solubility is used, a hardened product having low thermal expansion, flame retardancy, and heat resistance at high levels has not yet been obtained.

The improvement of the properties such as low water-absorbing property and heat resistance after moisture absorption has been still insufficient, although hardness has been improved by the prepolymerization proposed in Patent Document 8. Accordingly, it has been desired to further improve low water-absorbing property and heat resistance after moisture absorption. Furthermore, as proposed in Patent Documents 9 and 10, when the halogen-based compound is used, there is a risk that a harmful substance such as dioxin may be generated during combustion. Accordingly, it has been desired to improve flame retardancy without containing such a halogen-based compound.

The present invention has been made in view of the above circumstances, and it is an object of the present invention to provide a novel cyanate ester compound which has excellent solvent solubility and provides a hardened product having a low coefficiency of thermal expansion, and excellent flame retardancy and heat resistance, a hardened product thereof, a curable resin composition containing such a cyanate ester compound, a hardened product thereof, and a material for various applications containing the curable resin composition.

It is another object of the present invention to provide a curable resin composition for printed wiring boards which can realize a printed wiring board having not only low water-absorbing property but also excellent heat resistance after moisture absorption, a prepreg and laminate using the same, and a metal foil clad laminate and printed wiring board using the prepreg.

Solution to Problem

The present inventors found that a bifunctional cyanatophenyl-based cyanate ester compound having an adamantane skeleton has excellent solvent solubility and handling properties, and a curable resin composition using such a cyanate ester compound has a low coefficiency of thermal expansion, and can realize a hardened product or the like having excellent flame retardancy and heat resistance, thereby completing the present invention. The present inventors found that a printed wiring board having low water-absorbing property and also having excellent heat resistance after moisture absorption can be realized by using the curable resin composition containing such a cyanate ester compound, thereby completing the present invention. Specifically, the present invention is as follows.

[1] A cyanate ester compound represented by the following formula (1):

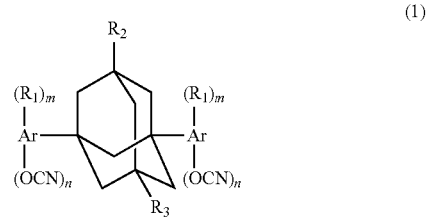

(1)

wherein Ar represents an aromatic ring; $R_1$ each independently represents a hydrogen atom, an alkyl group, or an aryl group; n each independently represents an integer of 1 to 3; m+n is the same as the total number of hydrogen atoms in a monovalent aromatic group containing the aromatic ring and the hydrogen atoms; $R_2$ represents a hydrogen atom (excluding a case where Ar represents a benzene ring; n each represents 1; $R_1$ represents a hydrogen atom; m each represents 4, and a cyanate group is bonded to the benzene ring in the 4-position relative to an adamantyl group), or an alkyl group having 1 to 4 carbon atoms; and $R_3$ represents a hydrogen atom or an alkyl group having 1 to 4 carbon atoms.

[2] The cyanate ester compound according to [1], wherein, in the formula (1), Ar represents a benzene ring; n represents 1; and $R_2$ represents a methyl group, an ethyl group, a propyl group, an isopropyl group, or a t-butyl group.

[3] The cyanate ester compound according to [1], wherein Ar represents a benzene ring; and n represents 2 or 3.

[4] The cyanate ester compound according to [1], wherein Ar represents an aromatic ring other than a benzene ring.

[5] A curable resin composition comprising a cyanate ester compound represented by the following formula (1):

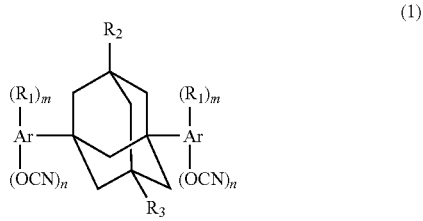

(1)

wherein Ar represents an aromatic ring; $R_1$ each independently represents a hydrogen atom, an alkyl group, or an aryl group; n represents an integer of 1 to 3; m+n represents an integer representing the total number of monovalent atoms and groups bonded to Ar; $R_2$ represents a hydrogen atom or an alkyl group having 1 to 4 carbon atoms; and $R_3$ represents a hydrogen atom or an alkyl group having 1 to 4 carbon atoms.

[6] The curable resin composition according to [5], further comprising one or more selected from the group consisting of a cyanate ester compound other than the cyanate ester compound represented by the formula (1), an epoxy resin, an oxetane resin, and a compound having a polymerizable unsaturated group.

[7] The curable resin composition according to [5] or [6], wherein, in the cyanate ester compound represented by the formula (1), Ar represents a benzene ring; n represents 1; and $R_2$ represents a methyl group, an ethyl group, a propyl group, an isopropyl group, or a t-butyl group.

[8] The curable resin composition according to [5] or [6], wherein, in the cyanate ester compound represented by the formula (1), Ar represents a benzene ring, and n represents 2 or 3.

[9] The curable resin composition according to [5] or [6], wherein, in the cyanate ester compound represented by the formula (1), Ar represents an aromatic ring other than a benzene ring.

[10] A hardened product obtained by curing the curable resin composition according to any one of [5] to [9].

[11] A prepreg for structural materials comprising a base material and the curable resin composition according to any one of [5] to [9] with which the base material is impregnated or coated.

[12] A sealing material comprising the curable resin composition according to any one of [5] to [9].

[13] A fiber-reinforced composite material comprising the curable resin composition according to any one of [5] to [9].

[14] An adhesive comprising the curable resin composition according to any one of [5] to [9].

[15] The curable resin composition according to any one of [5] to [9], wherein the curable resin composition is used for a printed wiring board.

[16] The curable resin composition according to [15], further comprising an epoxy resin.

[17] The curable resin composition according to [16], wherein a content of the cyanate ester compound represented by the formula (1) is 1 to 90 parts by mass based on 100 parts by mass of a resin solid content in the curable resin composition.

[18] The curable resin composition according to [16] or [17], further comprising an inorganic filler.

[19] The curable resin composition according to [18], wherein a content of the inorganic filler is 50 to 1600 parts by mass based on 100 parts by mass of a resin solid content in the curable resin composition.

[20] The curable resin composition according to any one of [16] to [19], further comprising one or more selected from the group consisting of a maleimide compound, a phenolic resin, and a cyanate ester compound other than the cyanate ester compound represented by the formula (1).

[21] The curable resin composition according to any one of [16] to [20], wherein the epoxy resin is one or more selected from the group consisting of a biphenyl aralkyl-based epoxy resin, a naphthylene ether-based epoxy resin, a multifunctional phenol-based epoxy resin, and a naphthalene-based epoxy resin.

[22] A prepreg comprising a base material and the curable resin composition according to any one of [15] to [21] with which the base material is impregnated or coated.

[23] A metal foil clad laminate comprising one or more of the prepreg according to [22] and a metallic foil disposed on one or both surfaces of the prepreg.

[24] A laminate comprising a support and a resin layer formed on a surface of the support by coating and drying of the curable resin composition according to any one of [15] to [21].

[25] A printed wiring board comprising an insulating layer and a conductor layer formed on a surface of the insulating layer, wherein the insulating layer comprises the curable resin composition according to any one of [15] to [21].

Advantageous Effects of Invention

The present invention can provide a novel cyanate ester compound which has excellent solvent solubility and provides a hardened product having a low coefficient of thermal expansion, and excellent flame retardancy and heat resistance, a hardened product thereof, a curable resin composition containing such a cyanate ester compound, a hardened product thereof, and a material for various applications containing the curable resin composition. The present invention can provide a curable resin composition for printed wiring boards which can realize a printed wiring board having not only low water-absorbing property but also excellent heat resistance after moisture absorption, a prepreg and laminate using the same, and a metal foil clad laminate and printed wiring board using the prepreg.

DESCRIPTION OF EMBODIMENTS

Figure 1:
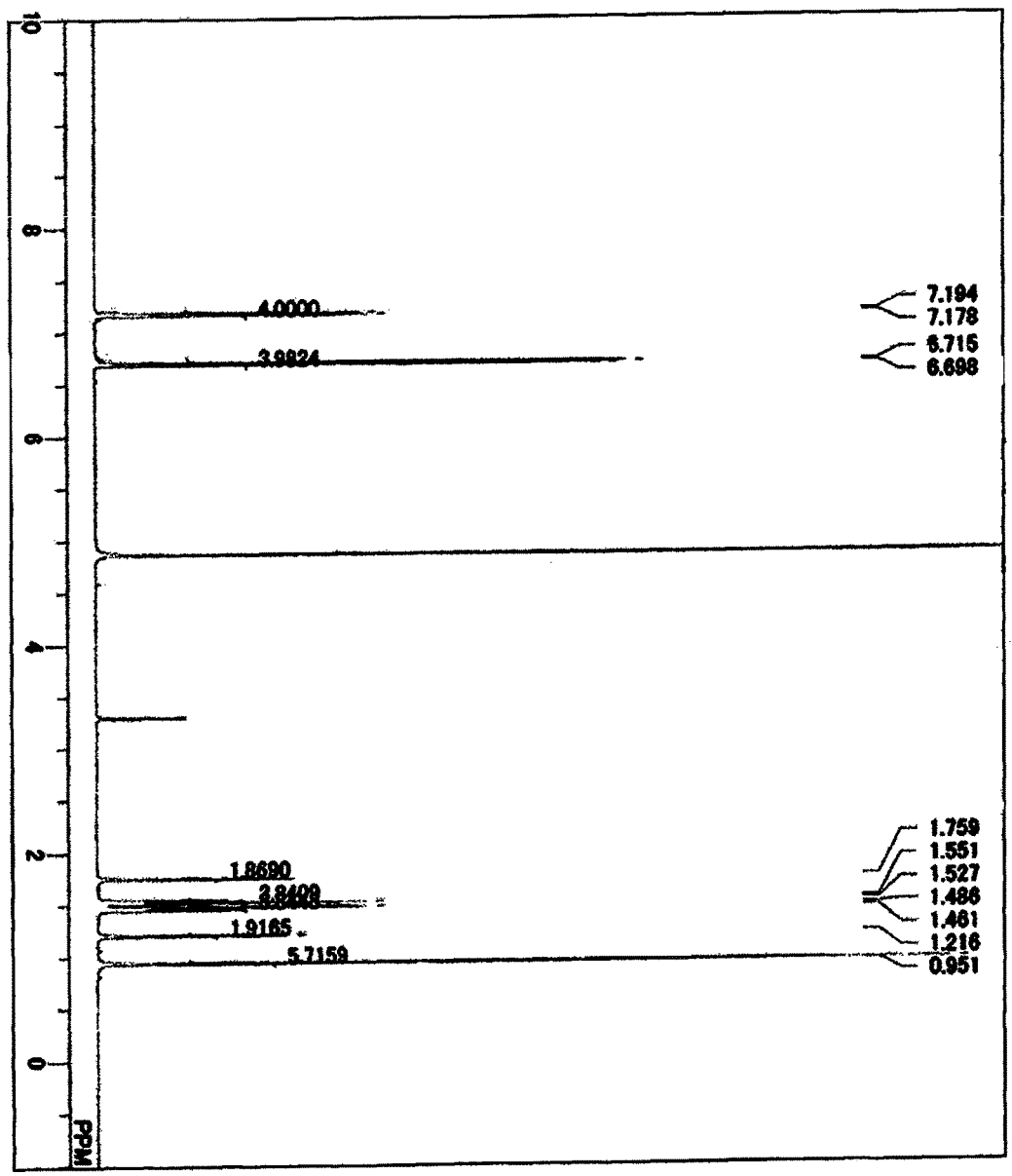
FIG. 1 is a $^1$H-NMR spectrum of a bisphenol compound AMTOH obtained in Example 1.

Hereinafter, embodiments for carrying out the present invention (hereinafter, referred to as "the present embodiment") will be described in detail. The following present embodiment is illustration for explaining the present invention, and the present invention is not limited only to the present embodiment.

A cyanate ester compound of the present embodiment is represented by the following formula (1).

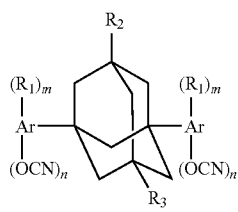

(1)

Herein, in the formula (1), Ar represents an aromatic ring; and $R_1$ each independently represents a hydrogen atom, an alkyl group, or an aryl group. n each independently represents an integer of 1 to 3; and m+n is the same as the total number of hydrogen atoms in a monovalent aromatic group containing the aromatic ring and the hydrogen atoms. $R_2$ represents a hydrogen atom (excluding a case where Ar represents a benzene ring; n each represents 1; $R_1$ represents a hydrogen atom; m each represents 4, and a cyanate group is bonded to the benzene ring in the 4-position relative to an adamantyl group), or an alkyl group having 1 to 4 carbon atoms. $R_3$ represents a hydrogen atom or an alkyl group having 1 to 4 carbon atoms.

A curable resin composition of the present embodiment contains the cyanate ester compound represented by the formula (1). Herein, in the formula (1), Ar represents an aromatic ring; and $R_1$ each independently represents a hydrogen atom, an alkyl group, or an aryl group. n each independently represents an integer of 1 to 3; m+n is the same as the total number of hydrogen atoms in a monovalent aromatic group containing the aromatic ring and the hydrogen atoms. $R_2$ represents a hydrogen atom or an alkyl group having 1 to 4 carbon atoms. $R_3$ represents a hydrogen atom or an alkyl group having 1 to 4 carbon atoms.

In another aspect of the present embodiment, a hardened product prepared by curing the curable resin composition, and a prepreg for structural materials, a sealing material, a fiber-reinforced composite material, and an adhesive which contain the curable resin composition are also provided.

<Cyanate Ester Compound>

The cyanate ester compound of the present embodiment is represented by the formula (1). In the formula (1), Ar represents an aromatic ring; $R_1$ each independently represents a hydrogen atom, an alkyl group, or an aryl group; n each independently represents an integer of 1 to 3; m+n is the same as the total number of hydrogen atoms in a monovalent aromatic group containing the aromatic ring and the hydrogen atoms. $R_2$ represents a hydrogen atom (excluding a case where Ar represents a benzene ring; n each represents 1; $R_1$ represents a hydrogen atom; m each represents 4, and a cyanate group is bonded to the benzene ring in the 4-position relative to an adamantyl group), or an alkyl group having 1 to 4 carbon atoms. $R_3$ represents a hydrogen atom or an alkyl group having 1 to 4 carbon atoms.

As long as Ar represents an aromatic ring, Ar may be a single ring, a condensed ring, or a ring assembly, and is not particularly limited. Ar is preferably selected from the group consisting of a benzene ring, a naphthalene ring, and a ring in which two benzene rings are singly-bonded.

$R_1$ each independently represents a hydrogen atom, an alkyl group, or an aryl group. Examples of the alkyl group include, but are not particularly limited to, preferably linear, branched, or cyclic alkyl groups having 1 to 8 carbon atoms, more preferably linear or branched alkyl groups having 1 to 8 carbon atoms, and still more preferably linear or branched alkyl groups having 1 to 4 carbon atoms, for example, a methyl group, an ethyl group, a propyl group, an isopropyl group, and a t-butyl group. Furthermore, examples of the aryl group of $R_1$ include, but are not particularly limited to, a phenyl group, a p-tolyl group, a naphthyl group, and an anthryl group. Among these, preferably, $R_1$ each independently represents a hydrogen atom or a linear alkyl group having 1 to 4 carbon atoms. Furthermore, n each independently represents preferably 1 to 2, and more preferably 1.

When Ar represents a benzene ring; n each represents 1; $R_1$ represents a hydrogen atom; m each represents 4, and a cyanate group is bonded to the benzene ring in the 4-position relative to an adamantyl group, $R_2$ represents an alkyl group having 1 to 4 carbon atoms. In the cases other than that, $R_2$ represents a hydrogen atom or an alkyl group having 1 to 4 carbon atoms. Examples of the alkyl group include, but are not particularly limited to, a methyl group, an ethyl group, a propyl group, an isopropyl group, and a t-butyl group. Among these, when Ar represents a benzene ring, $R_2$ is preferably a methyl group or an ethyl group. When Ar represents an aromatic ring other than a benzene ring, $R_2$ is preferably a hydrogen atom, a methyl group, or an ethyl group.

$R_3$ represents a hydrogen atom or an alkyl group having 1 to 4 carbon atoms. Examples of the alkyl group include, but are not particularly limited to, a methyl group, an ethyl group, a propyl group, an isopropyl group, and a t-butyl group. Among these, $R_3$ is preferably a hydrogen atom, a methyl group, and an ethyl group.

The cyanate ester compound of the present embodiment may be a cyanate ester compound in which Ar represents a benzene ring, n represents 1, and $R_2$ represents a methyl group, an ethyl group, a propyl group, an isopropyl group, or a t-butyl group; a cyanate ester compound in which Ar represents a benzene ring, and n represents 2 or 3; and a cyanate ester compound in which Ar represents an aromatic ring other than a benzene ring, in the formula (1).

Specific examples of the cyanate ester compound of the present embodiment include 1,3-bis(4-cyanatophenyl)-5-methyladamantane,
1,3-bis(4-cyanatophenyl)-5-ethyladamantane,
1,3-bis(4-cyanatophenyl)-5-propyladamantane,
1,3-bis(4-cyanatophenyl)-5-isopropyladamantane,
1,3-bis(4-cyanatophenyl)-5-t-butyladamantane,
1,3-bis(4-cyanatophenyl)-5,7-dimethyladamantane,
1,3-bis(4-cyanatophenyl)-5-methyl-7-ethyladamantane,
1,3-bis(4-cyanatophenyl)-5,7-diethyladamantane,
1,3-bis(4-cyanatophenyl)-5-methyl-7-propyladamantane,
1,3-bis(4-cyanatophenyl)-5-ethyl-7-propyladamantane,
1,3-bis(4-cyanatophenyl)-5,7-dipropyladamantane,
1,3-bis(4-cyanatophenyl)-5-methyl-7-isopropyladamantane,
1,3-bis(4-cyanatophenyl)-5-ethyl-7-isopropyladamantane,
1,3-bis(4-cyanatophenyl)-5-propyl-7-isopropyladamantane,
1,3-bis(4-cyanatophenyl)-5,7-diisopropyladamantane, 1,3-bis(4-cyanatophenyl)-5-methyl-7-t-butyladamantane,
1,3-bis(4-cyanatophenyl)-5-ethyl-7-t-butyladamantane,
1,3-bis(4-cyanatophenyl)-5-propyl-7-t-butyladamantane,
1,3-bis(4-cyanatophenyl)-5-isopropyl-7-t-butyladamantane,
1,3-bis(4-cyanatophenyl)-5,7-di-t-butyladamantane,
1,3-bis(3-methyl-4-cyanatophenyl)adamantane,
1,3-bis(3-methyl-4-cyanatophenyl)-5-methyladamantane,
1,3-bis(3-methyl-4-cyanatophenyl)-5-ethyladamantane,
1,3-bis(3-methyl-4-cyanatophenyl)-5-propyladamantane,
1,3-bis(3-methyl-4-cyanatophenyl)-5-isopropyladamantane,
1,3-bis(3-methyl-4-cyanatophenyl)-5-t-butyladamantane,
1,3-bis(3-methyl-4-cyanatophenyl)-5,7-dimethyladamantane,
1,3-bis(3-methyl-4-cyanatophenyl)-5-methyl-7-ethyladamantane,
1,3-bis(3-methyl-4-cyanatophenyl)-5,7-diethyladamantane,
1,3-bis(3-methyl-4-cyanatophenyl)-5-methyl-7-propyladamantane,
1,3-bis(3-methyl-4-cyanatophenyl)-5-ethyl-7-propyladamantane,
1,3-bis(3-methyl-4-cyanatophenyl)-5,7-dipropyladamantane,
1,3-bis(3-methyl-4-cyanatophenyl)-5-methyl-7-isopropyladamantane,
1,3-bis(3-methyl-4-cyanatophenyl)-5-ethyl-7-isopropyladamantane,
1,3-bis(3-methyl-4-cyanatophenyl)-5-propyl-7-isopropyladamantane,
1,3-bis(3-methyl-4-cyanatophenyl)-5,7-diisopropyladamantane,
1,3-bis(3-methyl-4-cyanatophenyl)-5-methyl-7-t-butyladamantane,
1,3-bis(3-methyl-4-cyanatophenyl)-5-ethyl-7-t-butyladamantane,
1,3-bis(3-methyl-4-cyanatophenyl)-5-propyl-7-t-butyladamantane,
1,3-bis(3-methyl-4-cyanatophenyl)-5-isopropyl-7-t-butyladamantane,
1,3-bis(3-methyl-4-cyanatophenyl)-5,7-di-t-butyladamantane,
1,3-bis(3,5-dimethyl-4-cyanatophenyl)adamantane,
1,3-bis(3,5-dimethyl-4-cyanatophenyl)-5-methyladamantane,
1,3-bis(3,5-dimethyl-4-cyanatophenyl)-5-ethyladamantane,
1,3-bis(3,5-dimethyl-4-cyanatophenyl)-5-propyladamantane,
1,3-bis(3,5-dimethyl-4-cyanatophenyl)-5-isopropyladamantane,
1,3-bis(3,5-dimethyl-4-cyanatophenyl)-5-t-butyladamantane,
1,3-bis(3,5-dimethyl-4-cyanatophenyl)-5,7-dimethyladamantane,
1,3-bis(3,5-dimethyl-4-cyanatophenyl)-5-methyl-7-ethyladamantane,
1,3-bis(3,5-dimethyl-4-cyanatophenyl)-5,7-diethyladamantane,
1,3-bis(3,5-dimethyl-4-cyanatophenyl)-5-methyl-7-propyladamantane,
1,3-bis(3,5-dimethyl-4-cyanatophenyl)-5-ethyl-7-propyladamantane,
1,3-bis(3,5-dimethyl-4-cyanatophenyl)-5,7-dipropyladamantane,
1,3-bis(3,5-dimethyl-4-cyanatophenyl)-5-methyl-7-isopropyladamantane,
1,3-bis(3,5-dimethyl-4-cyanatophenyl)-5-ethyl-7-isopropyladamantane,
1,3-bis(3,5-dimethyl-4-cyanatophenyl)-5-propyl-7-isopropyladamantane,
1,3-bis(3,5-dimethyl-4-cyanatophenyl)-5,7-diisopropyladamantane,
1,3-bis(3,5-dimethyl-4-cyanatophenyl)-5-methyl-7-t-butyladamantane,
1,3-bis(3,5-dimethyl-4-cyanatophenyl)-5-ethyl-7-t-butyladamantane,
1,3-bis(3,5-dimethyl-4-cyanatophenyl)-5-propyl-7-t-butyladamantane,
1,3-bis(3,5-dimethyl-4-cyanatophenyl)-5-isopropyl-7-t-butyladamantane,
1,3-bis(3,5-dimethyl-4-cyanatophenyl)-5,7-di-t-butyladamantane,
1,3-bis(3-phenyl-4-cyanatophenyl)adamantane,
1,3-bis(3-phenyl-4-cyanatophenyl)-5-methyladamantane,
1,3-bis(3-phenyl-4-cyanatophenyl)-5-ethyladamantane,
1,3-bis(3-phenyl-4-cyanatophenyl)-5-propyladamantane,
1,3-bis(3-phenyl-4-cyanatophenyl)-5-isopropyladamantane,
1,3-bis(3-phenyl-4-cyanatophenyl)-5-t-butyladamantane,
1,3-bis(3-phenyl-4-cyanatophenyl)-5,7-dimethyladamantane,
1,3-bis(3-phenyl-4-cyanatophenyl)-5-methyl-7-ethyladamantane,
1,3-bis(3-phenyl-4-cyanatophenyl)-5,7-diethyladamantane,
1,3-bis(3-phenyl-4-cyanatophenyl)-5-methyl-7-propyladamantane,
1,3-bis(3-phenyl-4-cyanatophenyl)-5-ethyl-7-propyladamantane,
1,3-bis(3-phenyl-4-cyanatophenyl)-5,7-dipropyladamantane,
1,3-bis(3-phenyl-4-cyanatophenyl)-5-methyl-7-isopropyladamantane,
1,3-bis(3-phenyl-4-cyanatophenyl)-5-ethyl-7-isopropyladamantane,
1,3-bis(3-phenyl-4-cyanatophenyl)-5-propyl-7-isopropyladamantane,
1,3-bis(3-phenyl-4-cyanatophenyl)-5,7-diisopropyladamantane,
1,3-bis(3-phenyl-4-cyanatophenyl)-5-methyl-7-t-butyladamantane,
1,3-bis(3-phenyl-4-cyanatophenyl)-5-ethyl-7-t-butyladamantane,
1,3-bis(3-phenyl-4-cyanatophenyl)-5-propyl-7-t-butyladamantane,
1,3-bis(3-phenyl-4-cyanatophenyl)-5-isopropyl-7-t-butyladamantane,
1,3-bis(3-phenyl-4-cyanatophenyl)-5,7-di-t-butyladamantane,
1,3-bis(3-cyclohexyl-4-cyanatophenyl)adamantane,
1,3-bis(3-cyclohexyl-4-cyanatophenyl)-5-methyladamantane,
1,3-bis(3-cyclohexyl-4-cyanatophenyl)-5-ethyladamantane,
1,3-bis(3-cyclohexyl-4-cyanatophenyl)-5-propyladamantane,
1,3-bis(3-cyclohexyl-4-cyanatophenyl)-5-isopropyladamantane,
1,3-bis(3-cyclohexyl-4-cyanatophenyl)-5-t-butyladamantane,
1,3-bis(3-cyclohexyl-4-cyanatophenyl)-5,7-dimethyladamantane,
1,3-bis(3-cyclohexyl-4-cyanatophenyl)-5-methyl-7-ethyladamantane,
1,3-bis(3-cyclohexyl-4-cyanatophenyl)-5,7-diethyladamantane,
1,3-bis(3-cyclohexyl-4-cyanatophenyl)-5-methyl-7-propyladamantane, 1,3-bis(3-cyclohexyl-4-cyanatophenyl)-5-ethyl-7-propyl-adamantane,
1,3-bis(3-cyclohexyl-4-cyanatophenyl)-5,7-dipropyladamantane,
1,3-bis(3-cyclohexyl-4-cyanatophenyl)-5-methyl-7-isopropyladamantane,
1,3-bis(3-cyclohexyl-4-cyanatophenyl)-5-ethyl-7-isopropyladamantane,
1,3-bis(3-cyclohexyl-4-cyanatophenyl)-5-propyl-7-isopropyladamantane,
1,3-bis(3-cyclohexyl-4-cyanatophenyl)-5,7-diisopropyladamantane,
1,3-bis(3-cyclohexyl-4-cyanatophenyl)-5-methyl-7-t-butyladamantane,
1,3-bis(3-cyclohexyl-4-cyanatophenyl)-5-ethyl-7-t-butyladamantane,
1,3-bis(3-cyclohexyl-4-cyanatophenyl)-5-propyl-7-t-butyladamantane,
1,3-bis(3-cyclohexyl-4-cyanatophenyl)-5-isopropyl-7-t-butyladamantane,
1,3-bis(3-cyclohexyl-4-cyanatophenyl)-5,7-di-t-butyladamantane,
1,3-bis(4-methyl-2-cyanatophenyl)adamantane,
1,3-bis(4-methyl-2-cyanatophenyl)-5-methyladamantane,
1,3-bis(4-methyl-2-cyanatophenyl)-5-ethyladamantane,
1,3-bis(4-methyl-2-cyanatophenyl)-5-propyladamantane,
1,3-bis(4-methyl-2-cyanatophenyl)-5-isopropyladamantane,
1,3-bis(4-methyl-2-cyanatophenyl)-5-t-butyladamantane,
1,3-bis(4-methyl-2-cyanatophenyl)-5,7-dimethyladamantane,
1,3-bis(4-methyl-2-cyanatophenyl)-5-methyl-7-ethyladamantane,
1,3-bis(4-methyl-2-cyanatophenyl)-5,7-diethyladamantane,
1,3-bis(4-methyl-2-cyanatophenyl)-5-methyl-7-propyladamantane,
1,3-bis(4-methyl-2-cyanatophenyl)-5-ethyl-7-propyladamantane,
1,3-bis(4-methyl-2-cyanatophenyl)-5,7-dipropyladamantane,
1,3-bis(4-methyl-2-cyanatophenyl)-5-methyl-7-isopropyladamantane,
1,3-bis(4-methyl-2-cyanatophenyl)-5-ethyl-7-isopropyladamantane,
1,3-bis(4-methyl-2-cyanatophenyl)-5-propyl-7-isopropyladamantane,
1,3-bis(4-methyl-2-cyanatophenyl)-5,7-diisopropyladamantane,
1,3-bis(4-methyl-2-cyanatophenyl)-5-methyl-7-t-butyladamantane,
1,3-bis(4-methyl-2-cyanatophenyl)-5-ethyl-7-t-butyladamantane,
1,3-bis(4-methyl-2-cyanatophenyl)-5-propyl-7-t-butyladamantane,
1,3-bis(4-methyl-2-cyanatophenyl)-5-isopropyl-7-t-butyladamantane,
1,3-bis(4-methyl-2-cyanatophenyl)-5,7-di-t-butyladamantane, and
1,3-bis(2,4-dicyanatophenyl)adamantane.

A method for obtaining the cyanate ester compound of the present embodiment is not in particularly limited. The cyanate ester compound is obtained by cyanation of a hydroxy group contained in a phenol compound represented by, for example, the following formula (2).

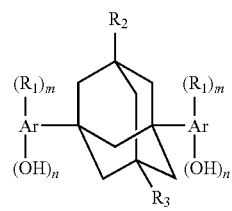

(2)

Herein, in the formula (2), Ar represents an aromatic ring; and $R_1$ each independently represents a hydrogen atom, an alkyl group, or an aryl group. n each independently represents an integer of 1 to 3; and m+n is the same as the total number of hydrogen atoms in a monovalent aromatic group containing the aromatic ring and the hydrogen atoms. $R_2$ represents a hydrogen atom (excluding a case where Ar represents a benzene ring; n each represents 1; $R_1$ represents a hydrogen atom; m each represents 4, and a hydroxy group is bonded to the benzene ring in the 4-position relative to an adamantyl group), or an alkyl group having 1 to 4 carbon atoms. $R_3$ represents a hydrogen atom or an alkyl group having 1 to 4 carbon atoms.

The phenol compound represented by the formula (2) can be obtained by methods described in, for example, U.S. Pat. No. 3,594,427, Japanese Patent Publication No. 4152501, and Japanese Patent Publication No. 4115269 or the like. Specific examples thereof include a method in which dibromo-dimethyladamantane is reacted with phenol, a method in which an adamantane diol is reacted with phenol in the presence of an acid catalyst, and a method in which an adamantane diol is reacted with a substituted phenol in the presence of an acid catalyst.

The method for cyanation of the hydroxy group contained in the phenol compound represented by the formula (2) is not particularly limited, and known methods can be applied. Specific examples thereof include: a method in which a phenol compound is reacted with a cyanogen halide in a solvent in the presence of a basic compound; a method in which a phenol compound is reacted with a cyanogen halide in a solvent in the presence of a base such that the cyanogen halide is always present in excess of the base (see U.S. Pat. No. 3,553,244); a method in which a tertiary amine used as a base in excess of a cyanogen halide is added to a phenol compound in the presence of a solvent, and thereafter the cyanogen halide is dropped or both the cyanogen halide and the tertiary amine are dropped into the phenol compound (see Japanese Patent Publication No. 3319061); a method in which a phenol compound, a trialkylamine, and a cyanogen halide are reacted in a continuous plug flow mode (see Japanese Patent Publication No. 3905559); a method in which a tert-ammonium halide produced as a by-product in reacting a phenol compound with a cyanogen halide in a nonaqueous solution in the presence of a tert-amine is treated with a cation and anion exchange pair (see Japanese Patent Publication No. 4055210); a method in which a phenol compound is reacted in the presence of a solvent separable from water by simultaneously adding a tertiary amine and a cyanogen halide, followed by washing with water and separation, and precipitation and purification from the obtained solution using a poor solvent of a secondary or tertiary alcohol or a hydrocarbon (see Japanese Patent Publication No. 2991054); and a method in which a phenol compound, a cyanogen halide, and a tertiary amine are reacted in a two-phase solvent of water and an organic solvent under acidic conditions (see Japanese Patent Publication No. 5026727). The cyanate ester compound of the present embodiment can be obtained using these methods.

When the method in which a phenol compound represented by the formula (2) is reacted with a cyanogen halide in the presence of a basic compound in a solvent is used, the phenol compound serving as a reaction base material is previously dissolved in a cyanogen halide solution or a basic compound solution, and the cyanogen halide solution and the basic compound solution are then brought into contact with each other.

Examples of the method for bringing a cyanogen halide solution into contact with a basic compound solution (contact method) include: (A) a method in which a basic compound solution is added dropwise to a cyanogen halide solution during stirring and mixing; (B) a method in which a cyanogen halide solution is added dropwise to a basic compound solution during stirring and mixing; and (C) a method in which a cyanogen halide solution and a basic compound solution are supplied continuously, alternatively, or simultaneously. Among the methods (A), (B), and (C), the method (A) can suppress side reactions and provide a higher-purity cyanate ester compound at a high yield, which is preferable.

The method for bringing a cyanogen halide solution into contact with a basic compound solution may be performed either in a semibatch form or in a continuous flow form.

Since the reaction can be completed with no remaining hydroxy groups contained in the phenol compound, and a higher-purity cyanate ester compound can be obtained at a high yield when the method (A) is particularly used, it is preferable that a basic compound is poured in portions. The number of such portions is not particularly limited. It is preferably 1 to 5 times. Either a single identical basic compound or different basic compounds may be used for each division.

Examples of the cyanogen halide include cyanogen chloride and cyanogen bromide. Cyanogen halide obtained by known producing methods such as a method in which a hydrogen cyanide or a metal cyanide is reacted with halogen may be used, or a commercially available cyanogen halide may be used. A reaction solution containing hydrogen cyanide or a cyanogen halide obtained by allowing a metal cyanide to react with halogen can also be used as it is.

The cyanogen halide is used in an amount of 0.5 to 5 mol, and preferably 1.0 to 3.5 mol, based on 1 mol of the hydroxy group of the phenol compound. This is because the yield of a cyanate ester compound is improved with no remaining unreacted phenol compounds.

Examples of the solvent used for the cyanogen halide solution include: ketone-based solvents such as acetone, methyl ethyl ketone, methyl isobutyl ketone, cyclohexanone, and cyclopentanone; aliphatic solvents such as n-hexane, cyclohexane, and isooctane; aromatic solvents such as benzene, toluene, and xylene; ether-based solvents such as diethyl ether, dimethyl cellosolve, diglyme, tetrahydrofuran, methyl tetrahydrofuran, dioxane, and tetraethylene glycol dimethyl ether; halogenated hydrocarbon-based solvents such as dichloromethane, chloroform, carbon tetrachloride, dichloroethane, trichloroethane, chlorobenzene, and bromobenzene; alcohol-based solvents such as methanol, ethanol, isopropanol, methyl cellosolve, and propylene glycol monomethyl ether; aprotic polar solvents such as N,N-dimethylformamide, N-methylpyrrolidone, 1,3-dimethyl-2-imidazolidone, and dimethyl sulfoxide; nitrile-based solvents such as acetonitrile and benzonitrile; nitro-based solvents such as nitromethane and nitrobenzene; ester-based solvents such as ethyl acetate and ethyl benzoate; hydrocarbon-based solvents such as cyclohexane; and water solvents. These can be used singly or in combination of two or more, depending on the type of a reaction substrate.

The basic compound which can be used may be either an organic base or an inorganic base. These are used singly or in combination of two or more.

Particularly, preferred examples of the organic base include tertiary amines such as trimethylamine, triethylamine, tri-n-butylamine, triamylamine, diisopropylethylamine, diethyl-n-butylamine, methyldi-n-butylamine, methylethyl-n-butylamine, dodecyldimethylamine, tribenzylamine, triethanolamine, N,N-dimethylaniline, N,N-diethylaniline, diphenylmethylamine, pyridine, diethylcyclohexylamine, tricyclohexylamine, 1,4-diazabicyclo[2.2.2]octane, 1,8-diazabicyclo[5.4.0]-7-undecene, and 1,5-diazabicyclo[4.3.0]-5-nonene. From the viewpoint obtaining a product of interest at a high yield, among these, trimethylamine, triethylamine, tri-n-butylamine, and diisopropylethylamine are more preferable, and triethylamine is particularly preferable.

The organic base is used in an amount of preferably 0.1 to 8 mol, and more preferably 1.0 to 3.5 mol, based on 1 mol of the hydroxy group of the phenol compound. This is because the yield of a cyanate ester compound is improved with no remaining unreacted phenol compounds.

Preferred examples of the inorganic base include alkali metal hydroxides. Examples of the alkali metal hydroxides include, but are not particularly limited to, industrially generally used sodium hydroxide, potassium hydroxide, and lithium hydroxide. From the viewpoint of inexpensive acquisition, sodium hydroxide is particularly preferable.

The inorganic base is used in an amount of preferably 1.0 to 5.0 mol, and more preferably 1.0 to 3.5 mol, based on 1 mol of the hydroxy group of the phenol compound. This is because the yield of a cyanate ester compound is improved with no remaining unreacted phenol compounds.

In the reaction for obtaining the cyanate ester compound of the present embodiment, the basic compound can be used in the form of a solution which is obtained by dissolving the basic compound in a solvent as described above. The solvent which can be used may be either an organic solvent or water.

The solvent used for the basic compound solution is used in an amount of preferably 0.1 to 100 parts by mass, and more preferably 0.5 to 50 parts by mass, based on 1 part by mass of the phenol compound when the phenol compound is dissolved in the basic compound solution. When at least a part of the phenol compound is not dissolved in the basic compound solution, the solvent is used in an amount of preferably 0.1 to 100 parts by mass, and more preferably 0.25 to 50 parts by mass, based on 1 part by mass of the basic compound.

The organic solvent in which the basic compound is dissolved is preferably used when the basic compound is an organic base. Examples of the organic solvent include: ketone-based solvents such as acetone, methyl ethyl ketone, and methyl isobutyl ketone; aromatic solvents such as benzene, toluene, and xylene; ether-based solvents such as diethyl ether, dimethyl cellosolve, diglyme, tetrahydrofuran, methyl tetrahydrofuran, dioxane, and tetraethylene glycol dimethyl ether; halogenated hydrocarbon-based solvents such as dichloromethane, chloroform, carbon tetrachloride, dichloroethane, trichloroethane, chlorobenzene, and bromobenzene; alcohol-based solvents such as methanol, ethanol, isopropanol, methyl cellosolve, and propylene glycol monomethyl ether; aprotic polar solvents such as N,N-dimethylformamide, N-methylpyrrolidone, 1,3-dimethyl-2-imidazolidone, and dimethyl sulfoxide; nitrile-based solvents such as acetonitrile and benzonitrile; nitro-based solvents such as nitromethane and nitrobenzene; ester-based solvents such as ethyl acetate and ethyl benzoate; and hydrocarbon-based solvents such as cyclohexane. These organic solvents can be appropriately selected depending on the types of the basic compound, reaction substrate, and solvent used in the reaction. These organic solvents can be used singly or in combination of two or more.

Water in which the basic compound is dissolved is preferably used, when the basic compound is an inorganic base, and is not particularly limited. The water may be tap water, distilled water, or deionized water. Distilled water and deionized water having a few impurities are preferable from the viewpoint of efficiently obtaining a cyanate ester compound of interest.

When the solvent used in the basic compound solution is water, a catalytic amount of an organic base as a surfactant is preferably used from the viewpoint of ensuring a more sufficient reaction rate. Among these, tertiary amines having relatively few side effects are preferable. The tertiary amines may be alkylamine, arylamine, or cycloalkylamine. Specific examples thereof include trimethylamine, triethylamine, tri-n-butylamine, triamyl amine, doisopropylethylamine, diethyl-n-butylamine, methyldi-n-butylamine, methylethyl-n-butylamine, dodecyldimethylamine, tribenzylamine, triethanolamine, N,N-dimethylaniline, N,N-diethylaniline, diphenylmethylamine, pyridine, diethylcyclohexylamine, tricyclohexylamine, 1,4-diazabicyclo[2.2.2]octane, 1,8-diazabicyclo[5.4.0]-7-undecene, and 1,5-diazabicyclo[4.3.0]-5-nonene. From the viewpoint of solubility in water and obtaining a product of interest at a higher yield, among these, trimethylamine, triethylamine, tri-n-butylamine, and diisopropylethylamine are more preferable, and triethylamine is particularly preferable. These are used singly or in combination of two or more.

The total amount of a solvent used in the cyanation step for obtaining the cyanate ester compound of the present embodiment is preferably 2.5 to 100 parts by mass, based on 1 part by mass of the phenol compound from the viewpoint of more uniformly dissolving the phenol compound and more efficiently producing the cyanate ester compound.

The pH of the reaction solution in the cyanation step for obtaining the cyanate ester compound of the present embodiment is not particularly limited. The reaction is preferably carried out while the pH of the reaction solution is kept at less than 7. By keeping the pH of the reaction solution at less than 7, the generation of by-products such as imidocarbonate and a polymer of a cyanate ester compound is further suppressed, and a cyanate ester compound can be more efficiently produced. In order to keep the pH of the reaction solution at less than 7, a method in which an acid is added to the reaction solution is preferable. More preferred examples are a method in which an acid is added to a cyanogen halide solution immediately before the cyanation step, and a method which includes adding an acid to the reaction system during the reaction, while appropriately measuring the pH of the reaction solution with a pH meter so as to keep the pH at less than 7. Examples of the acid used herein include inorganic acids such as hydrochloric acid, nitric acid, sulfuric acid and phosphoric acid, and organic acids such as acetic acid, lactic acid, and propionic acid.

From the viewpoint of suppressing the generation of by-products such as imidocarbonate, a polymer of a cyanate ester compound, and dialkyl cyanamide, the condensation of the reaction solution, and the vaporization of cyanogen chloride when the cyanogen chloride is used as a cyanogen halide, the reaction temperature applied in the cyanation step for obtaining the cyanate ester compound of the present embodiment is preferably −20° C. to +50° C., more preferably −15° C. to 15° C., and still more preferably −10° C. to 10° C.

The reaction pressure applied in the cyanation step for obtaining the cyanate ester compound of the present embodiment may be an ordinary pressure or a high pressure (specifically, a pressure higher than the ordinary pressure). Inert gas such as nitrogen, helium, and argon may be passed through the reaction system, as necessary.

The reaction time is not particularly limited. The pouring time in the case where the contact method is carried out by the method (A) and the method (B) and the contact time in the case of the method (C) are each preferably 1 minute to 20 hours, and more preferably 3 minutes to 10 hours. Thereafter, the reaction solution is preferably stirred for 10 minutes to 10 hours, while the reaction temperature is maintained.

By setting the reaction condition within the above-described range, a cyanate ester compound of interest is obtained with higher economical and industrial efficiency.

The degree of reaction progress in the cyanation step can be analyzed by liquid chromatography or an IR spectrum method or the like. Volatile components such as byproduct dicyan or dialkyl cyanamide can be analyzed by gas chromatography.

After completion of the reaction, an usual work-up operation, and as desired, separation and purification operations are carried out, so that a cyanate ester compound of interest can be isolated. Specifically, an organic solvent phase containing a cyanate ester compound is fractionated from the reaction solution, and thereafter, the organic solvent phase is washed with water and concentrated so that the cyanate ester compound can be precipitated or crystallized. Otherwise, after the organic solvent phase is washed with water, the organic solvent phase can be solvent-replaced. During the washing operation, in order to remove excessive amines, a method in which an acid aqueous solution such as diluted hydrochloric acid is used may also be adopted. In order to remove water content from the fully washed reaction solution, a drying operation may be carried out according to a common method using sodium sulfate or magnesium sulfate or the like. During the concentration and the solvent replacement, in order to suppress the polymerization of a cyanate ester compound, the reaction solution is heated to a temperature of 90° C. or lower under reduced pressure so as to distill away the organic solvent. A solvent having low solubility may be used in the precipitation or crystallization. For example, a method of dropping an ether-based solvent, a hydrocarbon-based solvent such as hexane, or an alcohol-based solvent into the reaction solution, or performing reverse pouring may be adopted. In order to wash the obtained crude product, a method of washing the concentrate of the reaction liquid or the precipitated crystals with an ether-based solvent, a hydrocarbon-based solvent such as hexane, or an alcohol-based solvent may be adopted. A method may be performed in which the reaction solution is concentrated to obtain crystals and the resultant crystals are again dissolved, followed by recrystallization. The reaction solution may simply be concentrated or cooled for crystallization.

The obtained cyanate ester compound can be identified by a known method such as NMR. The purity of the obtained cyanate ester compound can be analyzed by liquid chromatography or an IR spectrum method or the like. Volatile components including byproducts contained in the cyanate ester compound, such as dialkyl cyanamide, or remaining solvents, can be subjected to quantitative analysis by gas chromatography. Halogen compounds remaining in the cyanate ester compound can be identified with a liquid chromatography mass spectrometer. The halogen compounds can be subjected to quantitative analysis by potentiometric titration using a silver nitrate solution or ion chromatography after such compounds have been decomposed by a combustion method. The polymerization reactivity of the cyanate ester compound can be evaluated based on a gelatinization time by a hot plate method or a torque measurement method.

<Curable Resin Composition>

The curable resin composition of the present embodiment contains the cyanate ester compound of the present embodiment, and may contain a cyanate ester compound represented by the following formula (1).

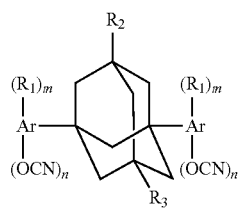

(1)

Herein, in the formula (1), Ar represents an aromatic ring; and $R_1$ each independently represents a hydrogen atom, an alkyl group, or an aryl group. n each independently represents an integer of 1 to 3; and m+n is the same as the total number of hydrogen atoms in a monovalent aromatic group containing the aromatic ring and the hydrogen atoms. $R_2$ represents a hydrogen atom or an alkyl group having 1 to 4 carbon atoms. $R_3$ represents a hydrogen atom or an alkyl group having 1 to 4 carbon atoms.

The cyanate ester compound contained in the curable resin composition of the present embodiment may be a cyanate ester compound in which Ar represents a benzene ring; n represents 1; and $R_2$ represents a methyl group, an ethyl group, a propyl group, an isopropyl group, or a t-butyl group, a cyanate ester compound in which Ar represents a benzene ring; and n represents 2 or 3, and a cyanate ester compound in which Ar represents an aromatic ring other than a benzene ring, in the formula (1).

For the cyanate ester compound contained in the curable resin composition of the present embodiment, Ar, $R_1$, n, m, and $R_3$ in the formula (1) have the same meanings as those in the cyanate ester compound of the present embodiment. Examples of the alkyl group in $R_2$ include, but are not particularly limited to, a methyl group, an ethyl group, a propyl group, an isopropyl group, and a t-butyl group. Among these, when Ar represents a benzene ring, $R_2$ is preferably a methyl group or an ethyl group. When Ar represents an aromatic ring other than a benzene ring, $R_2$ is preferably a hydrogen atom, a methyl group, or an ethyl group. Furthermore, specific example of the cyanate ester compound contained in the curable resin composition of the present embodiment include the cyanate ester compounds of the present embodiment exemplified above and 1,3-bis(4-cyanatophenyl)adamantine.

The curable resin composition may contain one or more selected from the group consisting of a cyanate ester compound other than the above-described cyanate ester compound (hereinafter, referred to as "another cyanate ester compound"), an epoxy resin, an oxetane resin, a benzoxazine compound, and a compound having a polymerizable unsaturated group in a range in which the expected properties are not impaired. Among these, from the viewpoint of more effectively and certainly exhibiting the function effect of the present invention, preferred are one or more selected from the group consisting of a cyanate ester compound, an epoxy resin, an oxetane resin, and a compound having a polymerizable unsaturated group.

Another cyanate ester compound is not particularly limited as long as it is a compound having, in one molecule thereof, an aromatic moiety in which at least one cyanate group is replaced. Examples thereof include a compound represented by the following formula (3).

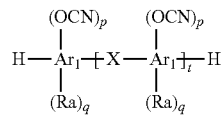

(3)

Herein, in the formula (3), $Ar_1$ represents a benzene ring, a naphthalene ring, or a ring in which two benzene rings are singly-bonded. A plurality of Ar1 may be the same or different from each other. Ra each independently represents a hydrogen atom, an alkyl group having 1 to 6 carbon atoms, an aryl group having 6 to 12 carbon atoms, an alkoxy group having 1 to 4 carbon atoms, or a group in which an alkyl group having 1 to 6 carbon atoms and an aryl group having 6 to 12 carbon atoms are mixed. The aromatic ring in Ra may have a substituent group, and the position of a substituent group in $Ar_1$ and Ra can optionally selected. p each independently represents an integer of 1 to 3. When $Ar_1$ is a benzene ring, q is 4-p. When $Ar_1$ is a naphthalene ring, q is 6-p. When $Ar_1$ is a ring in which two benzene rings are singly-bonded, q is 8-p. t represents an integer of 0 to 50, but another cyanate ester compound may be a mixture of compounds having different t. X represents a single bond, a divalent organic group having 1 to 20 carbon atoms (wherein a hydrogen atom may be replaced by a heteroatom), a divalent organic group having 1 to 10 nitrogen atoms (for example, —N—R—N— (herein, R represents an organic group)), a carbonyl group (—CO—), a carboxy group (—C(=O)O—), a carbonyl dioxide group (—OC(=O)O—), a sulfonyl group (—SO$_2$—), a divalent sulfur atom, or a divalent oxygen atom.

The alkyl group in Ra of the formula (3) may have a straight chain structure, a branched chain structure, or a cyclic structure (for example, a cycloalkyl group or the like).

The alkyl group in the formula (3) and the hydrogen atom in the aryl group in Ra may be replaced by: halogen atoms such as fluorine and chlorine; alkoxy groups such as a methoxy group and a phenoxy group; and a cyano group or the like.

Specific examples of the alkyl group include a methyl group, an ethyl group, a propyl group, an isopropyl group, an n-butyl group, an isobutyl group, a tert-butyl group, an n-pentyl group, a 1-ethylpropyl group, a 2,2-dimethylpropyl group, a cyclopentyl group, a hexyl group, a cyclohexyl group, and a trifluoromethyl group.

Specific examples of the aryl group include a phenyl group, a xylyl group, a mesityl group, a naphthyl group, a phenoxyphenyl group, an ethyiphenyl group, an o-, m- or p-fluorophenyl group, a dichlorophenyl group, a dicyanophenyl group, a trifluorophenyl group, a methoxyphenyl group, and an o-, m- or p-tolyl group. Furthermore, examples of the alkoxy group include a methoxy group, an ethoxy group, a propoxy group, an isopropoxy group, an n-butoxy group, an isobutoxy group, and a tert-butoxy group.

Specific examples of the divalent organic group having 1 to 20 carbon atoms in X of the formula (3) include: alkylene groups such as a methylene group, an ethylene group, a trimethylene group, and a propylene group; cycloalkylene groups such as a cyclopentylene group, a cyclohexylene group, and a trimethylcyclohexylene group; and divalent organic groups having an aromatic ring such as a biphenylmethylene group, a dimethylmethylene-phenylene-dimethylmethylene group, a fluorenediyl group, and a phthalidediyl group. The hydrogen atom in the divalent organic group may be replaced by halogen atoms such as fluorine and chlorine; alkoxy groups such as a methoxy group and a phenoxy group, or a cyano group, or the like.

Examples of the divalent organic group having 1 to 10 nitrogen atoms in X of the formula (3) include an imino group and a polyimide group.

Examples of X in the formula (3) include a divalent group represented by the following formula (4).

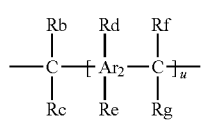
(4)

Herein, in the formula, Ar$_2$ represents a benzenetetrayl group, a naphthalenetetrayl group, or a biphenyltetrayl group, and may be the same or different from each other when u is 2 or more. Rb, Rc, Rf, and Rg each independently represent a hydrogen atom, an alkyl group having 1 to 6 carbon atoms, an aryl group having 6 to 12 carbon atoms, a trifluoromethyl group, or an aryl group having at least one phenolic hydroxy group. Rd and Re each independently represent a hydrogen atom, an alkyl group having 1 to 6 carbon atoms, an aryl group having 6 to 12 carbon atoms, an alkoxy group having 1 to 4 carbon atoms, or a hydroxy group. u represents an integer of 0 to 5.

Furthermore, examples of X in the formula (3) include a divalent group represented by the following formula.

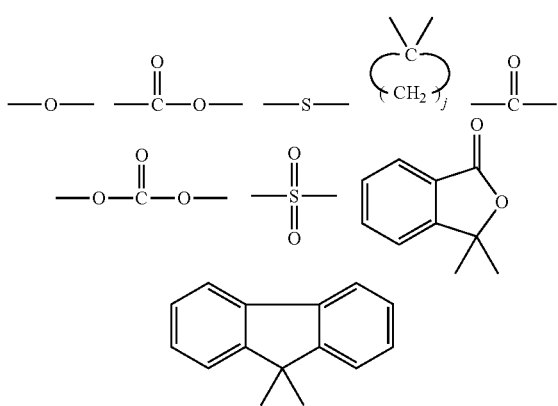

Herein, in the formula, j represents an integer of 4 to 7

Specific examples of Ar$_2$ in the formula (4) include a benzenetetrayl group in which two carbon atoms shown in the formula (4) are bonded to position 1,4 or position 1,3, a biphenyltetrayl group in which the two carbon atoms are bonded to position 4,4', position 2,4', position 2,2', position 2,3', position 3,3' or position 3,4', and a naphthalenetetrayl group in which the two carbon atoms are bonded to position 2,6, position 1,5, position 1,6, position 1,8, position 1,3 or position 1,4.

The alkyl group and the aryl group in Rb, Rc, Rd, Re, Rf, and Rg of the formula (4) have the same meanings as those in the formula (3).

Specific examples of the cyanate ester compound represented by the formula (3) include, but are not particularly limited to, cyanatobenzene, 1-cyanato-2-, 1-cyanato-3-, or 1-cyanato-4-methylbenzene, 1-cyanato-2-, 1-cyanato-3-, or 1-cyanato-4-methoxybenzene, 1-cyanato-2,3-, 1-cyanato-2,4-, 1-cyanato-2,5-, 1-cyanato-2,6-, 1-cyanato-3,4- or 1-cyanato-3,5-dimethylbenzene, cyanatoethylbenzene, cyanatobutylbenzene, cyanatooctylbenzene, cyanatononylbenzene, 2-(4-cyanatophenyl)-2-phenyl propane(4-α-cumylphenol cyanate), 1-cyanato-4-cyclohexylbenzene, 1-cyanato-4-vinylbenzene, 1-cyanato-2- or 1-cyanato-3-chlorobenzene, 1-cyanato-2,6-dichlorobenzene, 1-cyanato-2-methyl-3-chlorobenzene, cyanatonitrobenzene, 1-cyanato-4-nitro-2-ethylbenzene, 1-cyanato-2-methoxy-4-allylbenzene(eugenol cyanate), methyl(4-cyanatophenyl)sulfide, 1-cyanato-3-trifluoromethylbenzene, 4-cyanatobiphenyl, 1-cyanato-2- or 1-cyanato-4-acetylbenzene, 4-cyanatobenzaldehyde, 4-cyanatobenzoic acid methyl ester, 4-cyanatobenzoic acid phenyl ester, 1-cyanato-4-acetaminobenzene, 4-cyanatobenzophenone, 1-cyanato-2,6-di-tert-butylbenzene, 1,2-dicyanatobenzene, 1,3-dicyanatobenzene, 1,4-dicyanatobenzene, 1,4-dicyanato-2-tert-butylbenzene, 1,4-dicyanato-2,4-dimethylbenzene, 1,4-dicyanato-2,3,4-trimethylbenzene, 1,3-dicyanato-2,4,6-trimethylbenzene, 1,3-dicyanato-5-methylbenzene, 1-cyanato or 2-cyanatonaphthalene, 1-cyanato 4-methoxynaphthalene, 2-cyanato-6-methylnaphthalene, 2-cyanato-7-methoxynaphthalene, 2,2'-dicyanato-1,1'-binaphthyl, 1,3-, 1,4-, 1,5-, 1,6-, 1,7-, 2,3-, 2,6- or 2,7-dicyanatonaphthalene, 2,2'- or 4,4'-dicyanatobiphenyl, 4,4'-dicyanatooctafluorobiphenyl, 2,4'- or 4,4'-dicyanatodiphenylmethane, bis(4-cyanato-3,5-dimethylphenyl)methane, 1,1-bis(4-cyanatophenyl)ethane, 1,1-bis(4-cyanatophenyl)propane, 2,2-bis(4-cyanatophenyl)propane, 2,2-bis(4-cyanato-3-methylphenyl)propane, 2,2-bis(2-cyanato-5-biphenylyl)propane, 2,2-bis(4-cyanatophenyl) hexafluoropropane, 2,2-bis(4-cyanato-3, 5-dimethylphenyl) propane, 1,1-bis(4-cyanatophenyl)butane, 1,1-bis(4-cyanatophenyl)isobutane, 1,1-bis(4-cyanatophenyl)pentane, 1,1-bis(4-cyanatophenyl)-3-methylbutane, 1,1-bis(4-cyanatophenyl)-2-methylbutane, 1,1-bis(4-cyanatophenyl)-2,2-dimethylpropane, 2,2-bis(4-cyanatophenyl)butane, 2,2-bis (4-cyanatophenyl)pentane, 2,2-bis(4-cyanatophenyl) hexane, 2,2-bis(4-cyanatophenyl)-3-methylbutane, 2,2-bis (4-cyanatophenyl)-4-methylpentane, 2,2-bis(4-cyanatophenyl)-3,3-dimethylbutane, 3,3-bis(4-cyanatophenyl)hexane, 3,3-bis(4-cyanatophenyl)heptane, 3,3-bis(4-cyanatophenyl)octane, 3,3-bis(4-cyanatophenyl)-2-methylpentane, 3,3-bis(4-cyanatophenyl)-2-methylhexane, 3,3-bis(4-cyanatophenyl)-2,2-dimethylpentane, 4,4-bis(4-cyanatophenyl)-3-methylheptane, 3,3-bis(4-cyanatophenyl)-2-methylheptane, 3,3-bis(4-cyanatophenyl)-2,2-dimethylhexane, 3, 3-bis(4-cyanatophenyl)-2,4-dimethylhexane, 3,3-bis(4-cyanatophenyl)-2,2,4-trimethylpentane, 2,2-bis(4-cyanatophenyl)-1,1,1,3,3,3-hexafluoropropane, bis(4-cyanatophenyl)phenylmethane, 1,1-bis(4-cyanatophenyl)-1-phenyl ethane, bis(4-cyanatophenyl)biphenylmethane, 1,1-bis(4-cyanatophenyl)cyclopentane, 1,1-bis(4- cyanatophenyl)cyclohexane, 2,2-bis(4-cyanato-3-isopropylphenyl)propane, 1,1-bis(3-cyclohexyl-4-cyanatophenyl)cyclohexane, bis(4-cyanatophenyl)diphenylmethane, bis(4-cyanatophenyl)-2,2-dichloroethylene, 1,3-bis[2-(4-cyanatophenyl)-2-propyl]benzene, 1,4-bis[2-(4-cyanatophenyl)-2-propyl]benzene, 1,1-bis(4-cyanatophenyl)-3,3,5-trimethyl cyclohexane, 4-[bis(4-cyanatophenyl)methyl]biphenyl, 4,4-dicyanatobenzophenone, 1,3-bis(4-cyanatophenyl)-2-propen-1-one, bis(4-cyanatophenyl)ether, bis(4-cyanatophenyl)sulfide, bis(4-cyanatophenyl)sulfone, 4-cyanobenzoic acid-4-cyanatophenyl ester (4-cyanatophenyl-4-cyanatobenzoate), bis-(4-cyanatophenyl)carbonate, 1,3-bis(4-cyanatophenyl)adamantine, 3,3-bis(4-cyanatophenyl)isobenzofuran-1(3H)-one(phenolphthalein cyanate), 3,3-bis(4-cyanato-3-methylphenyl)isobenzofuran-1(3H)-one(o-cresolphthalei n cyanate), 9,9'-bis(4-cyanatophenyl)fluorene, 9,9-bis(4-cyanato-3-methylphenyl)fluorene, 9,9-bis(2-cyanato-5-biphenylyl)fluorene, tris(4-cyanatophenyl)methane, 1,1,1-tris(4-cyanatophenyl)ethane, 1,1,3-tris(4-cyanatophenyl)propane, α,α,α'-tris(4-cyanatophenyl)-1-ethyl-4-isopropylbenzene, 1,1,2,2-tetrakis(4-cyanatophenyl)ethane, tetrakis(4-cyanatophenyl)methane, 2,4,6-tris(N-methyl-4-cyanatoanilino)-1,3,5-triazine, 2,4-bis(N-methyl-4-cyanatoanilino)-6-(N-methyl anilino)-1,3,5-triazine, bis(N-4-cyanato-2-methylphenyl)-4,4'-oxydiphthalimide, bis(N-3-cyanato-4-methylphenyl)-4,4'-oxydiphthalimide, bis(N-4-cyanatophenyl)-4,4'-oxydiphthalimide, bis(N-4-cyanato-2-methylphenyl)-4,4'-(hexafluoroisopropylidene)diphthalimid e, tris(3,5-dimethyl-4-cyanatobenzyl)isocyanurate, 2-phenyl-3,3-bis(4-cyanatophenyl)phthalimidine, 2-(4-methylphenyl)-3,3-bis(4-cyanatophenyl)phthalimidine, 2-phenyl-3,3-bis(4-cyanato-3-methylphenyl)phthalimidine, 1-methyl-3,3-bis(4-cyanatophenyl)indolin-2-one, 2-phenyl-3,3-bis(4-cyanatophenyl)indolin-2-one, phenol novolac resins and cresol novolac resins (resins obtained by allowing phenol, alkyl-substituted phenol or halogen-substituted phenol to react with formaldehyde compounds such as formalin and paraformaldehyde in an acidic solution according to a known method), phenol aralkyl resins, cresol aralkyl resins, naphthol aralkyl resins, and biphenyl aralkyl resins (resins obtained by allowing a bishalogenomethyl compound represented by $Ar_3$—$(CH_2Y)_2$ to react with a phenol compound with an acidic catalyst or with no catalysts according to a known method, and resins obtained by allowing a bis(alkoxymethyl) compound represented by $Ar_3$—$(CH_2OR)_2$ or a bis(hydroxymethyl) compound represented by $Ar_3$—$(CH_2OH)_2$ to react with a phenol compound in the presence of an acidic catalyst), hydroxy-substituted aromatic compound denatured aromatic formaldehyde resins (resins obtained by allowing a xylene formaldehyde resin or a naphthalene formaldehyde resin or the like to react with a phenol compound in the presence of an acidic catalyst according to a known method), and resins obtained by cyanation of phenolic resins such as a phenol denatured dicyclopentadiene resin according to the same method as the above method. Another cyanate ester compounds can be used singly or in combination of two or more.

As an epoxy resin, a generally known epoxy resin can be used, as long as it is a compound having two or more epoxy groups in one molecule thereof. Examples of the epoxy resin include a bisphenol A-based epoxy resin, a bisphenol E-based epoxy resin, a bisphenol F-based epoxy resin, a bisphenol S-based epoxy resin, a bisphenol A novolac-based epoxy resin, a biphenyl-based epoxy resin, a phenol novolac-based epoxy resin, a cresol novolac-based epoxy resin, a xylene novolac-based epoxy resin, a naphthalene-based epoxy resin, an anthracene-based epoxy resin, a trifunctional phenol-based epoxy resin, a tetrafunctional phenol-based epoxy resin, triglycidyl isocyanulate, a glycidyl ester-based epoxy resin, an alicyclic epoxy resin, a dicyclopentadiene novolac-based epoxy resin, a biphenyl novolac-based epoxy resin, a phenol aralkyl novolac-based epoxy resin, a naphthol aralkyl novolac-based epoxy resin, an aralkyl novolac-based epoxy resin, a biphenyl aralkyl-based epoxy resin, a naphthol aralkyl-based epoxy resin, a dicyclopentadiene-based epoxy resin, a polyol-based epoxy resin, and an alicyclic epoxy resin or a halide thereof. These epoxy resins can be used singly or in combination of two or more.

As an oxetane resin, a generally known oxetane resin can be used. Examples of the oxetane resin include alkyloxetanes such as oxetane, 2-methyloxetane, 2,2-dimethyloxetane, 3-methyloxetane and 3,3-dimethyloxetane, 3-methyl-3-methoxymethyloxetane, 3,3'-di(trifluoromethyl)perfluoxetane, 2-chloromethyloxetane, 3,3-bis(chloromethyl)oxetane, as well as OXT-101 (manufactured by TOAGOSEI Co., Ltd., trade name) and OXT-121 (manufactured by TOAGOSEI Co., Ltd., trade name) as commercial items. These oxetane resins can be used singly or in combination of two or more.

A benzoxazine compound is preferably a compound having two or more dihydrobenzoxazine rings in one molecule thereof, and a generally known benzoxazine compound can be used. Examples of the benzoxazine compound include bisphenol A-based benzoxazine BA-BXZ (manufactured by KONISHI CHEMICAL IND CO., LTD., trade name), bisphenol F-based benzoxazine BF-BXZ (manufactured by KONISHI CHEMICAL IND CO., LTD., trade name), bisphenol S-based benzoxazine BS-BXZ (manufactured by KONISHI CHEMICAL IND CO., LTD., trade name), and phenolphthalein-based benzoxazine. These benzoxazine compounds can be used singly or in combination of two or more.

As a compound having a polymerizable unsaturated group, a generally known compound having a polymerizable unsaturated group can be used. Examples of the compound having a polymerizable unsaturated group include: vinyl compounds such as ethylene, propylene, styrene, divinylbenzene, and divinylbiphenyl; (meth)acrylates of monohydric or polyhydric alcohols, such as methyl(meth)acrylate, 2-hydroxyethyl(meth)acrylate, 2-hydroxypropyl(meth)acrylate, polypropylene glycol di(meth)acrylate, trimethylolpropane di(meth)acrylate, trimethylolpropane tri(meth)acrylate, pentaerythritol tetra(meth)acrylate, and dipentaerythritol hexa(meth)acrylate; epoxy(meth)acrylates such as bisphenol A-based epoxy(meth)acrylate and bisphenol F-based epoxy(meth)acrylate; a benzocyclobutene resin; and a (bis)maleimide resin. These compound having a polymerizable unsaturated group can be used singly or in combination of two or more. The above "(meth)acrylate" is a concept including acrylate, and methacrylate corresponding thereto.

The curable resin composition of the present embodiment may further contain a compound acting as a polymerization catalyst of a cyanate ester compound, an epoxy resin, an oxetane resin, or a compound having a polymerizable unsaturated group, in addition to the above described compounds and resins. Examples of such a polymerization catalyst include: metal salts such as zinc octylate, zinc naphthenate, cobalt naphthenate, copper naphthenate, and iron(III) acetylacetonate; phenol compounds such as octylphenol and nonylphenol; alcohols such as 1-butanol and 2-ethyl hexanol; imidazole derivatives such as 2-methylimidazole, 2-ethyl-4-methylimidazole, 2-phenylimidazole, 1-cyanoethyl-2-phenylimidazole, 1-cyanoethyl-2-ethyl-4-methylimidazole, 2-phenyl-4,5-dihydroxymethylimidazole, and 2-phenyl-4-methyl-5-hydroxymethylimidazole; amine compounds such as dicyan diamide, benzyldimethylamine, and 4-methyl-N,N-dimethylbenzylamine; and phosphorus compounds such as phosphine-based compounds and phosphonium-based compounds. There may be used, as the polymerization catalyst, peroxides such as epoxy-imidazole adduct-based compounds, benzoyl peroxide, p-chlorobenzoyl peroxide, di-t-butyl peroxide, diisopropyl peroxy carbonate, and di-2-ethylhexyl peroxy carbonate; and azo compounds such as azobisisobutyronitrile. As these polymerization catalysts, commercially available products may also be used. Examples of such commercially available polymerization catalysts include Ajicure PN-23 (manufactured by Ajinomoto Fine-Techno Co., Inc., trade name), Novacure HX-3721 (manufactured by Asahi Chemical Industry Co., Ltd., trade name), and Fujicure FX-1000 (manufactured by Fuji Kasei Co., Ltd., trade name). These polymerization catalysts can be used singly or in combination of two or more.

The curable resin composition of the present embodiment may further contain, as necessary, known additives such as a thermoplastic resin, an inorganic filler, a curing catalyst, a curing accelerator, a coloring pigment, a defoaming agent, a surface adjuster, a fire retardant, an ultraviolet absorber, an antioxidant, a photopolymerization initiator, a fluorescent brightener, a photosensitizer, a dye, a pigment, a thickener, a lubricant, a fluidity adjuster, a dispersant, a leveling agent, a brightening agent, a polymerization inhibitor, and a silane coupling agent. The curable resin composition of the present embodiment may contain a solvent, as necessary. These any given additives can be used singly or in combination of two or more.

As an inorganic filler, a generally known inorganic filler can be used. Examples of the inorganic filler include: silicates such as talc, fired clay, unfired clay, mica, E-glass, A-glass, NE-glass, C-glass, L-glass, D-glass, S-glass, M-glass G20, short glass fibers (including fine glass powders of E-glass, T-glass, D-glass, S-glass, and Q-glass or the like), hollow glass, and sphere glass; oxides such as titanium oxide, alumina, silica, fusion silica, zinc oxide, magnesium oxide, zirconium oxide, and molybdenum oxide; carbonates such as calcium carbonate, magnesium carbonate, and hydrotalcite; hydroxides such as aluminum hydroxide, magnesium hydroxide, and calcium hydroxide; sulfates or sulfites such as barium sulfate, calcium sulfate, and calcium sulfite; borates such as zinc borate, barium metaborate, aluminum borate, calcium borate, and sodium borate; nitrides such as aluminum nitride, boron nitride, silicon nitride, and carbon nitride; titanates such as strontium titanate and barium titanate; boehmite; zinc molybdate; and silicon composite powders and silicon resin powders. These inorganic fillers can be used singly or in combination of two or more.

As a solvent, a generally known solvent can be used. Examples of such a solvent include: ketone-based solvents such as acetone, methyl ethyl ketone, methyl isobutyl ketone, and cyclohexanone; cellosolve-based solvents such as propylene glycol monomethyl ether and propylene glycol monomethyl ether acetate; ester-based solvents such as methyl lactate, methyl acetate, ethyl acetate, butyl acetate, isoamyl acetate, ethyl lactate, methyl methoxypropionate, and methyl hydroxyisobutyrate; alcohol-based solvents such as methanol, ethanol, isopropanol, and 1-ethoxy-2-propanol; and aromatic hydrocarbons such as toluene, xylene, and anisole. These solvents can be used singly or in combination of two or more.

The curable resin composition of the present embodiment can be obtained by mixing the above-described cyanate ester compound, and as necessary, other cyanate ester compound, an epoxy resin, an oxetane resin, a benzoxazine compound and/or a compound having a polymerizable unsaturated group and various additives together with a solvent, using known mixers such as a high-speed mixer, a Nauta mixer, a ribbon-based blender, a kneader, an intensive mixer, a universal mixer, a dissolver, and a static mixer. Upon the mixing operation, a method in which a cyanate ester compound, other resins, various additives and a solvent are added is not particularly limited.

The hardened product can be obtained by curing the curable resin composition of the present embodiment with heat and light or the like. The hardened product can be obtained, for example, by melting the curable resin composition or dissolving it in a solvent, then pouring the resultant into a mold, and then curing it under usual conditions. In the case of thermal curing, the curing temperature is preferably set in a range of 120° C. to 300° C. from the viewpoint of further progression of curing and further prevention of deterioration in the obtained hardened product.

<Application of Curable Resin Composition>

A prepreg for structural materials of the present embodiment contains a base material and the curable resin composition with which the base material is impregnated or coated. The prepreg for structural materials can be produced by impregnating or coating an inorganic fiber base material and/or an organic fiber base material with the curable resin composition, and drying the inorganic fiber base material and/or the organic fiber base material as necessary.

The above base material is not particularly limited. Examples thereof include inorganic fiber base materials including glass fiber base materials such as glass woven cloths and glass nonwoven cloths, synthetic fiber base materials composed of woven cloths or nonwoven cloths containing, as main components, polyamide resin fibers such as polyamide resin fibers, aromatic polyamide resin fibers, and wholly aromatic polyamide resin fibers, polyester-based resin fibers such as polyester resin fibers, aromatic polyester resin fibers, and wholly aromatic polyester resin fibers, polyimide resin fibers, fluororesin fibers, or the like, and organic fiber base materials such as paper base materials, containing, as main components, kraft paper, cotton linter paper, and mixed paper of linters and kraft pulp, or the like. These known base materials can be appropriately selected and used according to performance required of the prepreg, for example, strength, a water absorption rate, and a coefficiency of thermal expansion or the like. The glass constituting the above glass fiber base materials is not particularly limited. Examples thereof include E-glass, C-glass, A-glass, S-glass, D-glass, NE-glass, T-glass, and H-glass.

For the method for producing the prepreg for structural materials, generally known methods can be appropriately applied, and the methods are not particularly limited. The prepreg can be produced by applying, for example, a method for preparing a resin varnish using the above-described curable resin composition, and immersing a base material in the resin varnish, a method for coating a base material with a resin varnish by various coaters, or a method for spraying by a spray. Among these, the method for immersing a base material in a resin varnish is preferable. By this, the impregnation properties of the resin composition into the base material can be improved. When a base material is immersed in a resin varnish, usual impregnation-coating equipment can be used. For example, a method for producing a prepreg by impregnating an inorganic fiber base material and/or an organic fiber base material with a resin composition varnish, drying the base material, and B-staging the base material can be applied.

The curable resin composition of the present embodiment can also be used in metal foil clad laminate and multilayer board applications. For the methods for producing these laminates or the like, generally known methods can be appropriately applied, and the methods are not particularly limited. For example, by laminating the above prepreg for structural materials and metallic foil, and hot-pressing them, a metal foil clad laminate can be obtained. At this time, the heating temperature is not particularly limited, and is usually preferably 65 to 300° C., and more preferably 120 to 270° C. The applied pressure is not particularly limited, and is usually preferably 2 to 5 MPa, and more preferably 2.5 to 4 MPa.

A sealing material of the present embodiment contains the curable resin composition of the present embodiment, and can be produced using the curable resin composition. For the method for producing a sealing material, generally known methods can be appropriately applied, and the methods are not particularly limited. For example, by mixing the above-described curable resin composition, and various additives known, for use in producing a sealing material, or a solvent, or the like, using a known mixer, the sealing material can be produced. For the method for adding a curable resin composition, various additives, and a solvent in mixing, generally known methods can be appropriately applied, and the methods are not particularly limited.

A fiber-reinforced composite material of the present embodiment contains the curable resin composition of the present embodiment, and can be produced using the curable resin composition and reinforcing fibers. As the reinforcing fibers contained in the fiber-reinforced composite material, for example, fibers such as carbon fibers, glass fibers, aramid fibers, boron fibers, PBO fibers, high strength polyethylene fibers, alumina fibers, and silicon carbide fibers can be used. The form and arrangement of the reinforcing fibers are not particularly limited, and can be appropriately selected from woven fabrics, nonwoven cloths, mats, knits, braids, unidirectional strands, rovings, and chopped, or the like. As the form of the reinforcing fibers, a preform (a laminate of woven ground cloths containing reinforcing fibers, or the laminate sewn and integrated by a stitching thread, or a fiber structure, such as a three-dimensional woven fabric or braided fabric) can also be applied. Specific examples of a method for producing the fiber-reinforced composite material include liquid composite molding methods, resin film infusion methods, filament winding methods, hand lay-up methods, and pultrusion methods. Among these, in a resin transfer molding method as one of liquid composite molding methods, various applications can be addressed because a material other than a preform, such as a metal plate, a foam core, or a honeycomb core, can be previously set in a mold. Therefore, the resin transfer molding method is preferably used when a composite material having a relatively complicated shape is mass-produced in a short time.

Since the cyanate ester compound of the present embodiment has excellent solvent solubility, the cyanate ester compound has excellent handling properties. Furthermore, a curable resin composition and a hardened product or the like which have excellent flame retardancy, heat resistance, and low thermal expansion can be realized by using the cyanate ester compound. Since the curable resin composition of the present embodiment has excellent low thermal expansion properties, flame retardancy, and heat resistance, the curable resin composition is extremely useful as a highly functional polymer material. Therefore, the curable resin composition is preferably used for electrical insulating materials, sealing materials, adhesives, lamination materials, resists, and buildup laminate materials, as well as fixing materials, structural members, reinforcing agents, and casting materials, or the like in the fields of civil engineering and construction, electrics and electronics, automobiles, railroads, ships, aircraft, sporting goods, arts and crafts, or the like as a material having excellent thermal, electrical, and mechanical properties. Among these, the curable resin composition is suitable for electrical insulating materials, semiconductor sealing materials, adhesives for electronic components, aircraft structural members, satellite structural members, and railroad car structural members of which low thermal expansion properties, flame resistance, and a high degree of mechanical strength are required.

<Curable Resin Composition for Printed Wiring Boards>

A curable resin composition for printed wiring boards of the present embodiment may contain the cyanate ester compound of the present embodiment, and may contain the cyanate ester compound (A) represented by the following formula (1).

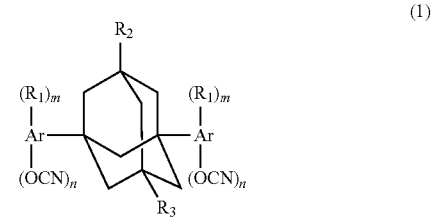

(1)

Herein, in the formula (1), Ar represents an aromatic ring; $R_1$ each independently represents a hydrogen atom, an alkyl group, or an aryl group. n each independently represents an integer of 1 to 3; and m+n is the same as the total number of hydrogen atoms in a monovalent aromatic group containing the aromatic ring and the hydrogen atoms. $R_2$ represents a hydrogen atom or an alkyl group having 1 to 4 carbon atoms. $R_3$ represents a hydrogen atom or an alkyl group having 1 to 4 carbon atoms. The cyanate ester compound (A) may be the same as that in the curable resin composition, and the detailed description thereof herein is omitted.

The content of the thus obtained cyanate ester compound (A) represented by the formula (1) in the curable resin composition for printed wiring boards of the present embodiment can be appropriately set according to desired properties, and is not particularly limited. The content of the cyanate ester compound (A) is preferably 1 to 90 parts by mass, and more preferably 5 to 70 parts by mass, based on 100 parts by mass of a resin solid content contained in the resin composition. The term "resin solid content in the resin composition" is used herein to mean resin components contained in the resin composition and components serving as resin components during heating, unless otherwise specified. For example, when the resin composition contains the cyanate ester compound (A), and an epoxy resin (B), a solvent, an inorganic filler (C), and a curing accelerator which will be described later, the term "resin solid content in the resin composition" is used herein to mean components except for a solvent, an inorganic filler (C), and a curing accelerator. The term "100 parts by mass of a resin solid content" is used to mean that a total of components except for a solvent, an inorganic filler (C), and a curing accelerator in the resin composition is 100 parts by mass.

The curable resin composition for printed wiring boards of the present embodiment preferably contains the cyanate ester compound (A) and an epoxy resin (B).

As the epoxy resin (B) of the present embodiment, a known epoxy resin can be appropriately used, as long as it is a compound having two or more epoxy groups in one molecule, and the type of the epoxy resin is not particularly limited. Specific examples of the epoxy resin include a bisphenol A-based epoxy resin, a bisphenol E-based epoxy resin, a bisphenol F-based epoxy resin, a bisphenol S-based epoxy resin, a phenol novolac-based epoxy resin, a bisphenol A novolac-based epoxy resin, a glycidyl ester-based epoxy resin, an aralkyl novolac-based epoxy resin, a biphenyl aralkyl-based epoxy resin, a naphthylene ether-based epoxy resin, a cresol novolac-based epoxy resin, a multifunctional phenol-based epoxy resin, a naphthalene-based epoxy resin, an anthracene-based epoxy resin, a naphthalene skeleton-modified novolac-based epoxy resin, a phenol aralkyl-based epoxy resin, a naphthol aralkyl-based epoxy resin, a dicyclopentadiene-based epoxy resin, a biphenyl-based epoxy resin, an alicyclic epoxy resin, a polyol-based epoxy resin, a phosphorus-containing epoxy resin, a compound obtained by epoxidation of a double bond of glycidyl amine, glycidyl ester, and butadiene or the like, and a compound obtained by a reaction of a hydroxyl group-containing silicon resin with epichlorohydrin. Among these epoxy resins, the biphenyl aralkyl-based epoxy resin, the naphthylene ether-based epoxy resin, the multifunctional phenol-based epoxy resin, and the naphthalene-based epoxy resin are preferable in terms of flame retardancy and heat resistance. These epoxy resins can be used singly or in combination of two or more.

The content of the epoxy resin (B) of the present embodiment can be appropriately set according to desired properties, and is not particularly limited. The content of the epoxy resin is preferably 10 to 99 parts by mass, and more preferably 10 to 70 parts by mass, based on 100 parts by mass of a resin solid content in the resin composition.

The resin composition of the present embodiment can also contain an inorganic filler (C). As the inorganic filler (C), a known inorganic filler can be appropriately used, and the type of the inorganic filler (C) is not particularly limited. As the inorganic filler (C), inorganic fillers generally used for laminate applications can be preferably used. Specific examples of the inorganic filler (C) include silicas, such as natural silica, fusion silica, synthetic silica, amorphous silica, AEROSIL, and hollow silica, white carbon, titanium white, zinc oxide, magnesium oxide, zirconium oxide, boron nitride, aggregated boron nitride, silicon nitride, aluminum nitride, barium sulfate, aluminum hydroxide, heat-treated products of aluminum hydroxide (products obtained by heat-treating aluminum hydroxide to decrease some of the water of crystallization), boehmite, metal hydrates such as magnesium hydroxide, molybdenum compounds such as molybdenum oxide and zinc molybdate, zinc borate, zinc stannate, alumina, clay, kaolin, talc, calcined clay, calcined kaolin, calcined talc, mica, E-glass, A-glass, NE-glass, C-glass, L-glass, D-glass, S-glass, M-glass G20, glass short fibers (including glass fine powders of E-glass, T-glass, D-glass, S-glass, and Q-glass, or the like), hollow glass, and spherical glass. These inorganic fillers (C) are used singly or in combination of two or more. The resin composition contains the inorganic filler (C), which can particularly have more excellent low water-absorbing property, heat resistance after moisture absorption, and flame retardancy.

The resin composition of the present embodiment may contain the inorganic filler (C), as well as organic fillers such as styrene-based, butadiene-based and acryl-based rubber powders, coreshell-based rubber powders, silicon resin powders, silicon rubber powders, and silicon composite powders. These organic fillers can be used singly or in combination of two or more.

When the resin composition of the present embodiment contains the inorganic filler (C), the content of the inorganic filler (C) can be appropriately set according to desired properties, and is not particularly limited. The content thereof is preferably 50 to 1600 parts by mass, more preferably 60 to 600 parts by mass, and still more preferably 70 to 300 parts by mass, based on 100 parts by mass of a resin solid content in the resin composition. When the resin composition contains an organic filler, the total amount of the organic filler and inorganic filler (C) is preferably 50 to 1600 parts by mass, more preferably 60 to 600 parts by mass, and still more preferably 70 to 300 parts by mass, based on 100 parts by mass of a resin solid content in the resin composition.

Herein, at least one of the silane coupling agent and the moisture dispersant is preferably combined with the inorganic filler (C) from the viewpoint of increasing an interaction with a resin component to increase the mechanical strengths of the laminate, metal foil clad laminate, and printed wiring board. As the silane coupling agent, a silane coupling agent generally used for the surface treatment of inorganic matters can be preferably used. The type of the silane coupling agent is not particularly limited. Specific examples of the silane coupling agent include: aminosilane-based coupling agents such as γ-aminopropyltriethoxysilane and N-β-(aminoethyl)-γ-aminopropyltrimethoxysilane; epoxysilane-based coupling agents such as γ-glycidoxypropyltrimethoxysilane and β-(3,4-epoxycyclohexyl)ethyltrimethoxysilane; vinylsilane-based coupling agents such as γ-methacryloxypropyltrimethoxysilane and vinyl-tri(p-methoxyethoxy)silane; cationic silane coupling agents such as N-β-(N-vinylbenzylaminoethyl)-γ-aminopropyltrimethoxysilane hydrochloride; and phenylsilane-based coupling agents. These silane coupling agents can be used singly or in combination of two or more. As the moisture dispersant, a moisture dispersant generally used for coating can be preferably used. The type of the moisture dispersant is not particularly limited. Preferably, a copolymer-based moisture dispersant is used as the silane coupling agent, and specific examples of such a moisture dispersant include Disperbyk-110, 111, 161 and 180, BYK-W996, BYK-W9010, BYK-W903, and BYK-W940 (all of which are trade names), which are manufactured by BYK-Chemie Japan K.K. These moisture dispersants can be used singly or in combination of two or more.

The resin composition of the present embodiment contains the cyanate ester compound (A) and the epoxy resin (B), and has thermosetting properties. The resin composition may contain a curing accelerator for appropriately adjusting the curing rate of a resin component as necessary. As the curing accelerator, a curing accelerator generally used for a cyanate ester compound or an epoxy resin or the like can be preferably used. The type of the curing accelerator is not particularly limited. Specific examples of the curing accelerator include: organic metal salts such as zinc octylate, zinc naphthenate, cobalt naphthenate, copper naphthenate, iron (III) acetylacetonate, nickel octylate, and manganese octylate; phenol compounds such as phenol, xylenol, cresol, resorcin, catechol, octylphenol, and nonylphenol; alcohols such as 1-butanol and 2-ethyl hexanol; imidazoles such as 2-methylimidazole, 2-ethyl-4-methylimidazole, 2-phenylimidazole, 1-cyanoethyl-2-phenylimidazole, 1-cyanoethyl-2-ethyl-4-methylimidazole, 2-phenyl-4,5-dihydroxymethylimidazole, and 2-phenyl-4-methyl-5-hydroxymethylimidazole; derivatives such as the carboxylates of these imidazoles, or the acid anhydride adducts thereof; amines such as dicyan diamide, benzyldimethylamine, and 4-methyl-N,N-dimethylbenzylamine; phosphorus compounds such as a phosphine compound, a phosphine oxide compound, a phosphonium compound, and a diphosphine compound; peroxides such as an epoxy-imidazole adduct compound, benzoyl peroxide, p-chlorobenzoyl peroxide, di-t-butyl peroxide, diisopropyl peroxy carbonate, and di-2-ethylhexyl peroxy carbonate; and azo compounds such as azobisisobutyronitrile. These curing accelerators can be used singly or in combination of two or more.

The used amount of the curing accelerator can be appropriately adjusted, taking into consideration the hardness of the resin, and the viscosity of the resin composition, or the like, and is not particularly limited. In general, the content is about 0.005 to 10 parts by mass based on 100 parts by mass of a resin solid content in the resin composition.

The resin composition of the present embodiment may contain one or more selected from the group consisting of a cyanate ester compound other than the cyanate ester compound (A) represented by the formula (1), a maleimide compound, a phenolic resin, an oxetane resin, a benzoxazine compound, and a compound having a polymerizable unsaturated group in a range in which the expected properties are not impaired. In these, preferred are one or more compounds selected from the group consisting of a maleimide compound, a phenolic resin, and a cyanate ester compound other than the cyanate ester compound (A) represented by the formula (1) from the viewpoint of heat resistance.

The cyanate ester compound other than the cyanate ester compound (A) represented by the formula (1) may be the same as the cyanate ester compound other than the cyanate ester compound represented by the formula (1) described in the description of the curable resin composition, and the detailed description thereof herein is omitted.

As the maleimide compound, a generally known maleimide compound can be used, as long as it is a compound having one or more maleimide groups in one molecule thereof. Examples of the maleimide compound include, but are not particularly limited to, 4,4-diphenylmethane bismaleimide, phenylmethanemaleimide, m-phenylene bismaleimide, 2,2-bis(4-(4-maleimidephenoxy)-phenyl)propane, 3,3-dimethyl-5,5-diethyl-4,4-diphenylmethane bismaleimide, 4-methyl-1,3-phenylene bismaleimide, 1,6-bismaleimide-(2,2,4-trimethyl)hexane, 4,4-diphenylether bismaleimide, 4,4-diphenylsulfone bismaleimide, 1,3-bis(3-maleimidephenoxy)benzene, 1,3-bis(4-maleimidephenoxy)benzene, polyphenylmethane maleimide, and prepolymers of these maleimide compounds, or prepolymers of the maleimide compounds and amine compounds. These maleimide compounds can be used singly or in combination of two or more.

A phenolic resin having two or more hydroxyl groups in one molecule thereof is preferable, and a generally known phenolic resin can be used. Examples of the phenolic resin include, but are not particularly limited to, a bisphenol A-based phenolic resin, a bisphenol E-based phenolic resin, a bisphenol F-based phenolic resin, a bisphenol S-based phenolic resin, a phenol novolac resin, a bisphenol A novolac-based phenolic resin, a glycidyl ester-based phenolic resin, an aralkyl novolac-based phenolic resin, a biphenyl aralkyl-based phenol resin, a cresol novolac-based phenolic resin, a multifunctional phenolic resin, a naphthol resin, a naphthol novolac resin, a multifunctional naphthol resin, an anthracene-based phenolic resin, a naphthalene skeleton-modified novolac-based phenolic resin, a phenol aralkyl-based phenolic resin, a naphthol aralkyl-based phenolic resin, a dicyclopentadiene-based phenolic resin, a biphenyl-based phenolic resin, an alicyclic phenolic resin, a polyol-based phenolic resin, a phosphorus-containing phenolic resin, and a hydroxyl group-containing silicon resin. These phenolic resins can be used singly or in combination of two or more.

An oxetane resin, a benzoxazine compound, and a compound having a polymerizable unsaturated group may be the same as those described in the description of the curable resin composition, and the detailed description thereof herein is omitted.

Furthermore, the curable resin composition for printed wiring boards of the present embodiment can contain other thermosetting resins, thermoplastic resins and the oligomers thereof, various polymer compounds such as elastomers, flame-retardant compounds, and various additives or the like in a range in which the expected properties are not impaired. These compounds are not particularly limited as long as they are generally used. Examples of the flame-retardant compound include: bromine compounds such as 4,4'-dibromobiphenyl; nitrogen compounds such as phosphoric acid ester, melamine phosphate, a phosphorus-containing epoxy resin, melamine, and benzoguanamine; and oxazine ring-containing compounds and silicone compounds. Examples of the various additives include an ultraviolet absorber, an antioxidant, a photopolymerization initiator, a fluorescent brightener, a photosensitizer, a dye, a pigment, a thickener, a fluidity adjuster, a lubricant, a defoaming agent, a dispersant, a leveling agent, a brightening agent, and a polymerization inhibitor. These can be used singly or in combination of two or more as required.

The curable resin composition for printed wiring boards of the present embodiment can contain an organic solvent as necessary. In this case, the resin composition of the present embodiment can be used as an aspect (that is, a solution or a varnish) in which at least a part, and preferably all of the above-described various resin components are dissolved in an organic solvent, or compatible with it. As such an organic solvent, a known organic solvent can be appropriately used, as long as it is able to dissolve or be compatible with at least a part of, and preferably all of the above-described various resin components, and the type of the organic solvent is not particularly limited. Specific examples of the organic solvent include: ketones such as acetone, methyl ethyl ketone, methyl isobutyl ketone; cellosolve solvents such as propylene glycol monomethyl ether and propylene glycol monomethyl ether acetate; ester solvents such as ethyl lactate, methyl acetate, ethyl acetate, butyl acetate, isoamyl acetate, ethyl lactate, methyl methoxypropionate, and methyl hydroxyisobutyrate; polar solvents including amides such as dimethylacetamide and dimethylformamide; and non-polar solvents including aromatic hydrocarbons such as toluene and xylene. These can be used singly or in combination of two or more.

The curable resin composition for printed wiring boards of the present embodiment can be used as an insulating layer of a printed wiring board, and a semiconductor packaging material, for example. For example, a prepreg can be produced by impregnating or coating a base material with a solution prepared by dissolving the resin composition of the present embodiment in a solvent, followed by drying.

A build-up film or dry film solder resist can be produced by applying a solution prepared by dissolving the resin composition for printed wiring boards of the present embodiment in a solvent onto a removable plastic film used as a base material, followed by drying. Herein, the solvent can be dried by heating it at a temperature of, for example, 20 to 150° C. for 1 to 90 minutes. The resin composition can be used in an uncured state in which only the solvent is dried away from the resin composition, or as necessary, the film can be used in a semicured (B-staged) state.

Hereinafter, the prepreg of the present embodiment will be described in detail. The prepreg of the present embodiment is prepared by impregnating or coating a base material with the curable resin composition for printed wiring boards of the present embodiment. Specifically, the prepreg includes a base material and the curable resin composition for printed wiring boards of the present embodiment with which the base material is impregnated or coated. A method for producing a prepreg is not particularly limited as long as the method combines the resin composition of the present embodiment with a base material to produce a prepreg. For example, the prepreg of the present embodiment can be produced by impregnating or coating a base material with the resin composition of the present embodiment, and then drying the resulting base material at 120 to 220° C. for about 2 to 15 minutes so as to semicure the base material. During this operation, the amount of a resin composition attached to a base material, namely, the amount of a resin composition to a total amount of a prepreg after being semicured (when the resin composition contains the inorganic filler (C), the amount of the inorganic filler (C) is also contained in the amount of the resin composition) is preferably in a range of 20 to 99% by mass.

As a base material used when the prepreg of the present embodiment is produced, a known base material used for various printed wiring board materials can be used. Examples of such a base material include, but are not particularly limited to, woven cloths of glass fibers of E-glass, D-glass, L-glass, S-glass, T-glass, Q-glass, UN-glass, NE-glass, and spherical glass or the like, inorganic fibers of materials other than glass such as quartz, organic fibers of polyimide, polyamide, and polyester or the like, and liquid crystal polyester. As the shape of the base material, woven cloth, nonwoven cloth, roving, chopped strand mat, and surfacing mat or the like are known, and any may be used. The base materials can be used singly or in combination of two or more. The thickness of the base material is not particularly limited. If the base material is used for a laminate, the thickness of the base material is preferably set in a range of 0.01 to 0.2 mm. From the viewpoint of dimension stability, a woven fabric, on which a ultra-opening treatment or a weather-stripping treatment has been performed, is particularly preferable. Furthermore, a glass woven fabric, the surface of which has been treated with a silane coupling agent, such as an epoxysilane treatment or an aminosilane treatment, is preferable from the viewpoint of heat resistance after moisture absorption. A liquid crystal polyester woven fabric is preferable in terms of electrical properties.

The metal foil clad laminate of the present embodiment is produced by placing one or more of the above described prepreg and then disposing a metallic foil on one or both surfaces of the prepreg, followed by laminate molding. Specifically, the metal foil clad laminate of the present embodiment includes one or more of the above described prepreg and a metallic foil disposed on one or both surfaces of the prepreg. Specifically, one of the above described prepreg is placed or a plurality of the above described prepregs are laminated on one another, and a metallic foil such as a copper or aluminum foil is disposed on one or both surfaces of the layer, followed by laminate molding, so as to produce a metal foil clad laminate. The metallic foil used herein is not particularly limited, as long as it is used as a material for printed wiring boards. A copper foil such as a rolled copper foil or an electrolytic copper foil is preferable. The thickness of the metallic foil is not particularly limited, and is preferably 2 to 70 µm, and more preferably 3 to 35 µm. With regard to molding conditions, means for laminates and multilayer boards used for usual printed wiring boards can be applied. For example, a multistage pressing machine, a multistage vacuum pressing machine, a continuous molding machine, or an autoclave molding machine or the like is used, and laminate molding is carried out at a temperature of 180 to 350° C., for a heating time of 100 to 300 minutes, and at a surface pressure of 20 to 100 kg/cm$^2$, so as to produce the metal foil clad laminate of the present embodiment. The above described prepreg is combined with a circuit board used for inner layer, which has been produced separately. The combined product can be subjected to laminate molding, so as to produce a multilayer board. Specifically, the multilayer board includes the prepreg and a circuit board used for inner layer, and is obtained by laminating one or two or more of the prepregs and one or two or more of the circuit boards used for inner layer. As a method for producing such a multilayer board, for example, a copper foil (for example, a thickness of 35 µm) is disposed on both surfaces of one of the above described prepreg, and the resultant is then subjected to laminate molding under the above described conditions. Thereafter, an internal circuit is formed, and the formed circuit is then subjected to a blackening treatment to form an internal circuit board. Thereafter, this internal circuit boards and the above described prepregs are disposed alternatively on a one-by-one base. Furthermore, a copper foil is disposed as an outermost layer, and the thus obtained layer is subjected to laminate molding under the above described conditions, and preferably under vacuum. Thereby, a multilayer board can be produced.

The metal foil clad laminate of the present embodiment can be preferably used as a material for printed wiring boards. The printed wiring board can be produced according to an usual method, and the production method is not particularly limited. Hereinafter, an example of the method for producing the printed wiring board will be described. First, the above described metal foil clad laminate such as a copper-clad laminate is prepared. Subsequently, the surface of the metal foil clad laminate is subjected to etching processing to form an internal circuit, thereby producing an internal base board. The surface of the internal circuit of this internal base board is subjected to a surface treatment for enhancing adhesion strength, as necessary. Thereafter, a predetermined number of the above described prepregs are laminated on the surface of the internal circuit, and further, a metallic foil used as an external circuit is laminated on the outside thereof. The resultant is subjected to integral molding by heating and compression. As such, a multilayer laminate in which an insulating layer containing a base material and a hardened product of a thermosetting resin composition is formed between an internal circuit and a metallic foil used as an external circuit, is produced. Subsequently, this multilayer laminate is subjected to hole-making processing of making a through hole or a via hole, and a plated metal coating for conducting the internal circuit and the metallic foil used as an external circuit to the wall surface of the hole is then formed. The metallic foil used as an external circuit is subjected to etching processing to form an external circuit, thereby producing a printed wiring board.

The printed wiring board obtained as described above includes an insulating layer and a conductor layer formed on the surface of the insulating layer, wherein the insulating layer contains the curable resin composition for printed wiring boards of the present embodiment. Specifically, the insulating layer in the printed wiring board is derived from the above-described prepreg of the present embodiment (a base material, and the resin composition of the present embodiment with which the base material is impregnated or coated) and the resin composition layer of the above-described metal foil clad laminate of the present embodiment (a layer containing the resin composition of the present embodiment).

The laminate of the present embodiment can be obtained by applying a solution in which the curable resin composition for printed wiring boards of the present embodiment is dissolved in a solvent or compatible with it, to a support, followed by drying. Specifically, a laminate of the present embodiment includes a support and a resin phase disposed on the surface of the support and prepared by coating and drying of the resin composition. Examples of the support used herein include, but are not particularly limited to, a polyethylene film, a polypropylene film, a polycarbonate film, a polyethylene terephthalate film, an ethylene tetrafluoroethylene copolymer film, demolding films obtained by applying a demolding agent on the surface of these films, organic film base materials such as a polyimide film, conductor foils such as a copper foil and an aluminum foil, platy supports such as a glass plate, an SUS plate, and FRP. Examples of the applying method include a method which includes applying a solution in which the curable resin composition of the present embodiment is dissolved in a solvent or compatible with it, onto a support using a bar coater, a die coater, a doctor blade, and a baker applicator or the like. After applying, the support may be removed or etched from the laminate obtained by drying, so as to form a monolayer sheet (resin sheet). The above described resin composition of the present embodiment is dissolved in a solvent or compatible with it, to obtain a solution. The obtained solution is then supplied to a mold having a sheet-like cavity, and then molded into a sheet by drying it or the like, so that a monolayer sheet (resin sheet) can also be obtained without using supports.

In the production of the monolayer or laminate of the present embodiment, drying conditions applied upon the removal of the solvent are not particularly limited. From the viewpoint of suppressing the residual solvent in the curable resin composition for printed wiring boards and the curing of the resin composition, drying is preferably carried out at a temperature of 20 to 200° C. for 1 to 90 minutes. The thickness of the resin layer in the monolayer or laminate of the present embodiment can be adjusted depending on the concentration of the solution of the resin composition of the present embodiment and the thickness of the solution coated, and the thickness of the resin layer is not particularly limited. In general, the thickness of the resin layer is preferably 0.1 to 500 μm. The residual solvent during drying is more easily suppressed by setting the thickness to 500 μm or less.

According to the present invention, a prepreg, a laminate (resin composite sheet), and a metal foil clad laminate or the like which have low water-absorbing property as well as excellent heat resistance after moisture absorption can be realized, and a high-performance printed wiring board can be realized. According to a preferred aspect of the present invention, a curable resin composition for printed wiring boards containing only a non-halogen compound (in other words, a resin composition containing no halogen compound, namely, a non-halogen resin composition), a prepreg, a laminate, and a metal foil clad laminate or the like can also be realized, and the industrial practicability of the resin composition is extremely high.

EXAMPLES

Hereinafter, the present invention will be described more in detail in Examples. However, the present invention is not particularly limited by the following Examples.

Example 1

Synthesis of
1,3-Bis(4-Cyanatophenyl)-5,7-Dimethyladamantane
(Hereinafter, Abbreviated as "AMTCN")

AMTCN represented by the following formula (5) was synthesized as described later.

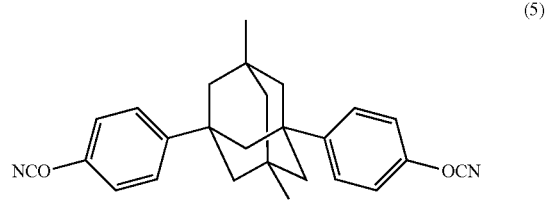

(5)

Synthesis of
1,3-Bis(4-Hydroxyphenyl)-5,7-Dimethyladamantane
(Hereinafter, Abbreviated as "AMTOH")

First, AMTOH represented by the following formula (6) was synthesized.

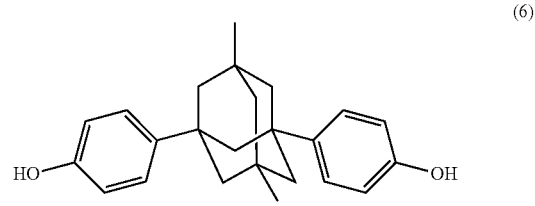 [SMILES: CC12CC3(C)CC(c4ccc(O)cc4)(C1)CC(c1ccc(O)cc1)(C2)C3]

(6)

Specifically, 166.0 g (0.85 mol) of 5,7-dimethyladamantane-1,3-diol and 644.4 g (6.85 mol) of phenol were added into a reaction system under a nitrogen gas flow, and the obtained mixture was then melted by heating at 80° C. Then, while stirring, 81.5 g (0.85 mol) of methanesulfonic acid was added to the reaction mixture. Thereafter, the temperature was increased to 100° C., and the reaction was then carried out at the same temperature for 4 hours. Subsequently, 600 mL of water and 300 mL of methanol were added to the reaction solution, and the obtained mixture was then cooled to 4° C. in an ice bath. The reaction mixture was stirred at the same temperature for 1 hour. Thereafter, a precipitate was collected by filtration, and the obtained crystal was repeatedly washed with 500 mL of hot water at 70° C. four times. After washing, the crystal was dissolved in a mixed solvent of 1100 mL of ethyl acetate and 500 mL of toluene. The obtained solution was washed with 500 mL of a 0.5%-by-mass NaOH aqueous solution three times, and thereafter, washing with 500 mL of water was repeatedly carried out until the pH of a water phase became neutral. After completion of the water washing, an organic phase was concentrated and dried under reduced pressure to obtain a solid. The obtained solid was dissolved in 1000 mL of ethyl acetate at 70° C. To the obtained solution, 2000 mL of heptane was added at room temperature, and the obtained mixture was then stirred for 10 minutes to obtain a precipitate. The precipitate was collected by filtration, and then washed with 600 mL of heptane twice. Finally, the resultant was dried at 90° C. for 14 hours, to obtain 183.5 g of AMTOH (white solid). The structure of the AMTOH was identified by NMR. The $^1$H-NMR spectrum is shown in FIG. 1.

$^1$H-NMR: (500 MHz, Methanol-d3)

δ (ppm)=0.95 (s, 6H), 1.22 (s, 2H), 1.46 (d, J=12.5 Hz, 4H), 1.54 (d, J=12.5 Hz, 4H), 1.76 (s, 2H), 6.71 (m, J=8.5 Hz, 4H), 7.18 (m, J=8.5 Hz, 4H)

<Synthesis of AMTCN>

Next, 550 g (OH group equivalent: 174.3 g/eq., 3.16 mol in terms of hydroxy groups) of the AMTOH obtained by the above described method and 319.3 g (3.16 mol, in an amount of 1.0 mol based on 1 mol of hydroxy group of the AMTOH) of triethylamine were dissolved in 3300 g of dichloromethane, and the obtained solution was defined as a solution 1.

The solution 1 was poured into a mixture of 329.8 g (5.37 mol, in an amount of 1.7 mol based on 1 mol of hydroxy group of the AMTOH) of cyanogen chloride, 770 g of dichloromethane, 479.5 g (4.73 mol, in an amount of 1.5 mol based on 1 mol of hydroxy group of the AMTOH) of 36% hydrochloric acid and 2973 g of water under stirring, while keeping the solution temperature at −2 to −0.5° C. over 82 minutes. After completion of the pouring of the solution 1, the reaction solution was stirred at the same temperature as described above for 30 minutes, and a solution (solution 2) prepared by dissolving 319.3 g (3.16 mol, in an amount of 1.0 mol based on 1 mol of hydroxy group of the AMTOH) of triethylamine in 319.3 g of dichloromethane was poured into the reaction solution over 42 minutes. After completion of the pouring of the solution 2, the reaction solution was stirred at the same temperature as described above for 30 minutes, and the reaction was then terminated.

Thereafter, the reaction solution was left at rest, so that an organic phase was separated from a water phase. The obtained organic phase was washed with 2000 g of 0.1 N hydrochloric acid, and then with 2000 g of water five times. The electrical conductivity of the wastewater at the 5th water washing was 20 µS/cm, and it was confirmed that an ionic compound to be removed was sufficiently removed by washing with water.

Figure 2:
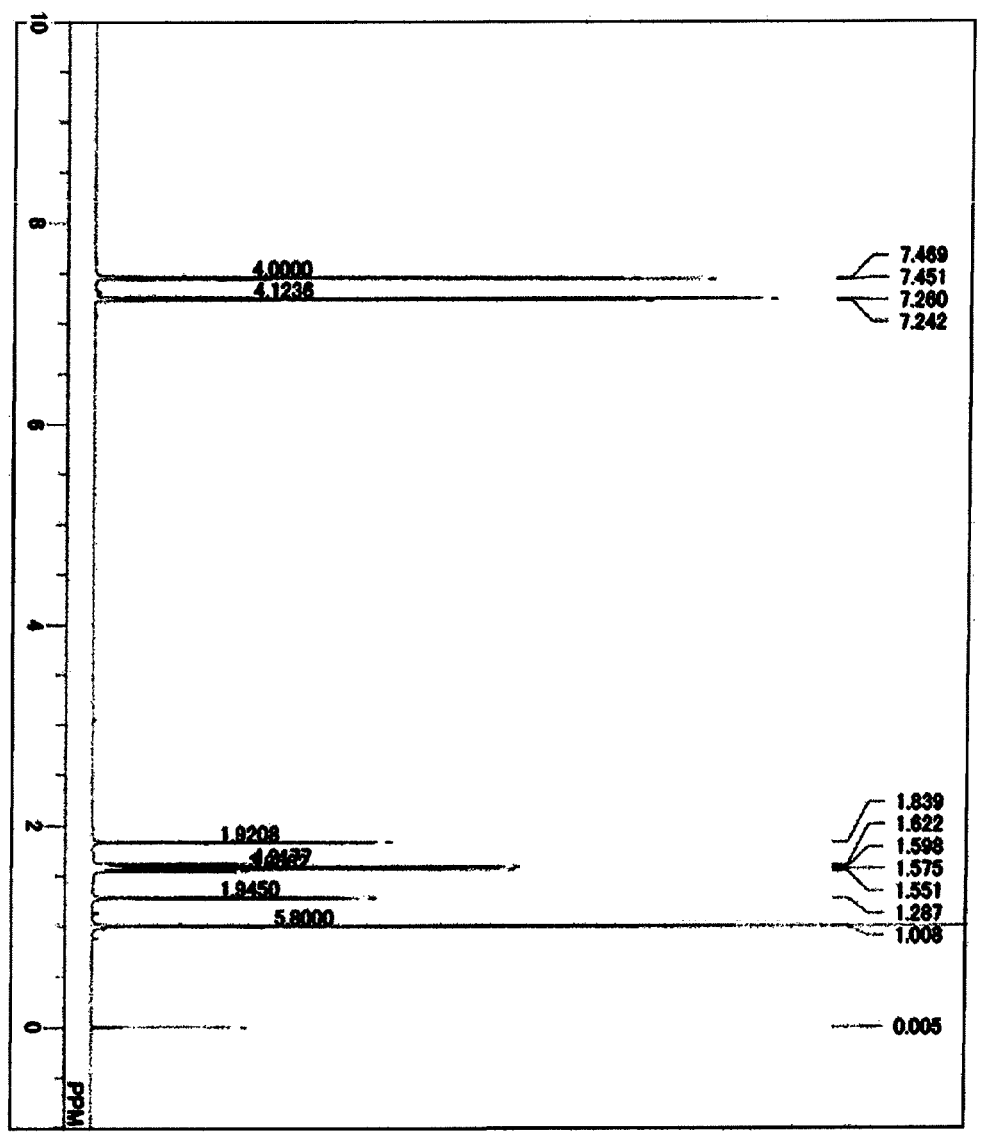
FIG. 2 is a $^1$H-NMR spectrum of a cyanate ester compound AMTCN obtained in Example 1.

After completion of the water washing, the organic phase was concentrated under reduced pressure, and finally, it was concentrated and dried at 90° C. for 1 hour to obtain 436 g of the cyanate ester compound AMTCN (white crystal) of interest. The structure of the obtained cyanate ester compound AMTCN was identified by NMR. The $^1$H-NMR spectrum is shown in FIG. 2.

$^1$H-NMR: (500 MHz, CDCl3)

δ (ppm)=1.01 (s, 6H), 1.29 (s, 2H), 1.56 (d, J=12 Hz, 4H), 1.61 (d, J=12 Hz, 4H), 1.84 (s, 2H), 7.51 (m, J=9.0 Hz, 4H), 7.60 (m, J=9.0 Hz, 4H)

Figure 3:
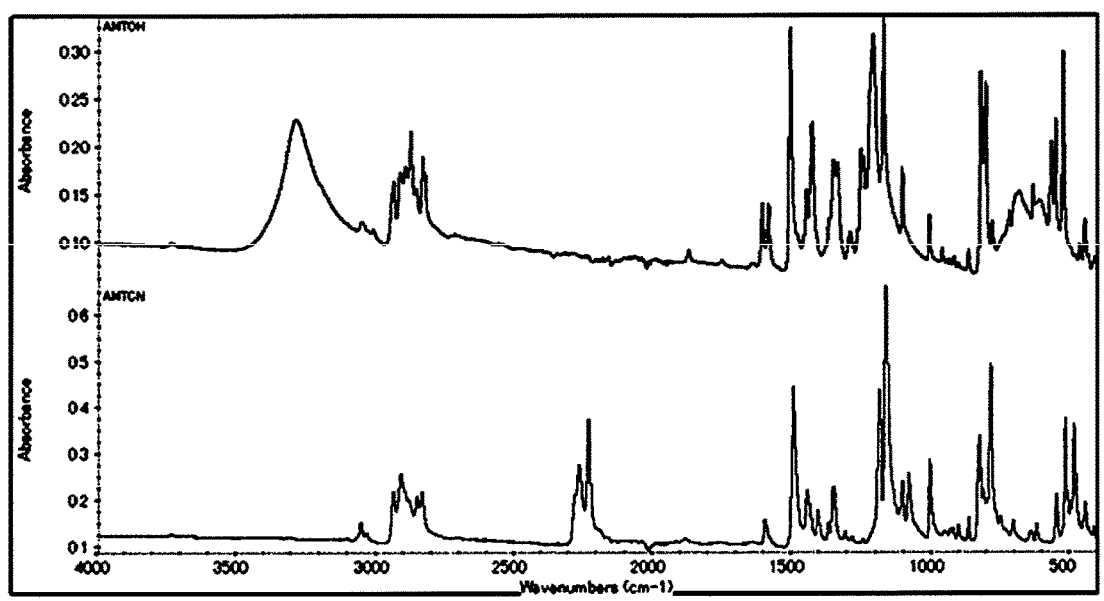
FIG. 3 is an FT-IR chart of a cyanate ester compound AMTCN obtained in Example 1.

The IR spectrum of the AMTCN exhibited absorptions of 2237 cm$^{-1}$ and 2271 cm$^{-1}$ (cyanate ester group) and did not exhibit the absorption of hydroxy group. The IR chart is shown in FIG. 3.

It was possible to dissolve 50% by mass or more of the AMTCN in methyl ethyl ketone (MEK) at 25° C.

Example 2

Synthesis of 1,3-Bis(3-Methyl-4-Cyanatophenyl)-5,7-Dimethyladamantane (Hereinafter, Abbreviated as "AMTcCN")

AMTcCN represented by the following formula (7) was synthesized as described later.

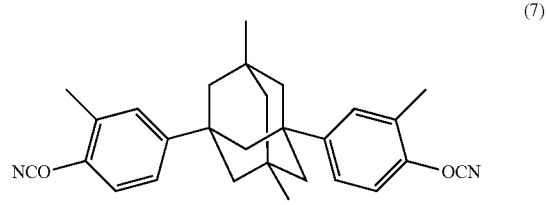

(7)

Synthesis of 1,3-Bis(3-Methyl-4-Hydroxyphenyl)-5,7-Dimethyladamantane (Hereinafter, Abbreviated as "AMTcOH")

First, AMTcOH represented by the following formula (8) was synthesized.

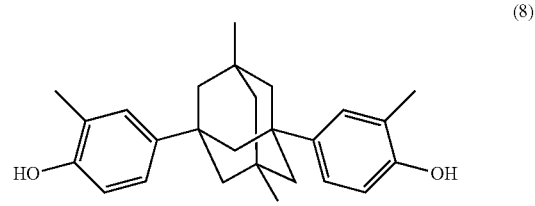 [SMILES: Cc1cc(C23CC4(C)CC(C)(C2)CC(c2ccc(O)c(C)c2)(C4)C3)ccc1O]

(8)

Figure 4:
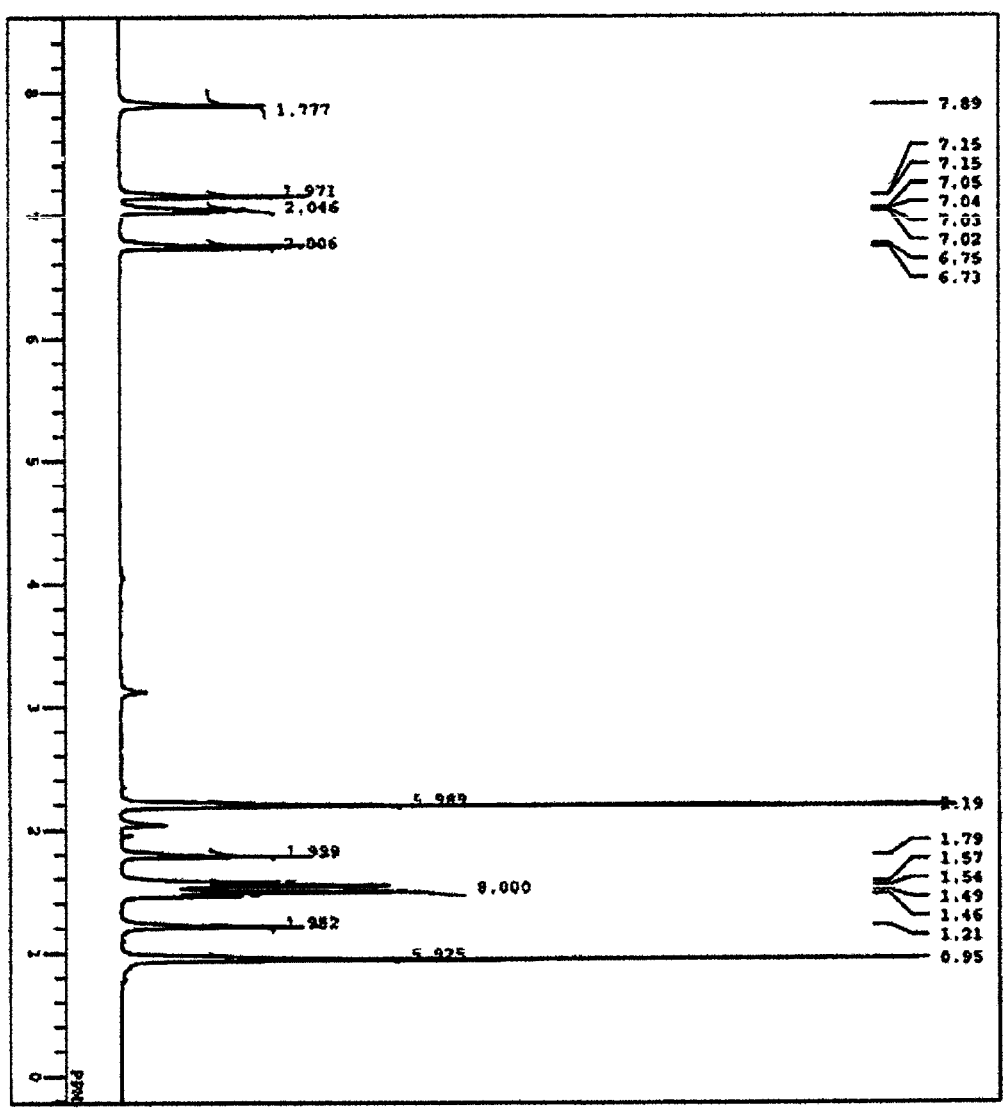
FIG. 4 is a $^1$H-NMR spectrum of a bisphenol compound AMTcOH obtained in Example 2.

Specifically, nitrogen gas was circulated for nitrogen substitution in a 2 L-separable flask, and 104.68 g of 1,3-dihydroxy-5,7-dimethyladamantane was added into a reaction system. Furthermore, 460.67 g of o-cresol was added into the reaction system. The obtained mixture was stirred while being heated to increase the solution temperature to 80° C. When the solution temperature reached 80° C., the pouring of methanesulfonic acid was initiated. As a result of the pouring of 53.59 g of methanesulfonic acid over 10 minutes, the solution temperature was increased to 90° C. by the generation of heat. The reaction was continued at 90° C. for 4 hours. When 400 mL of hot water was added to the reaction solution at 65 to 70° C. after 4 hours, and 800 mL of heptane was subsequently added to the reaction solution at room temperature, the solution temperature was decreased to 65° C. The solution was then allowed to spontaneously cool for 30 minutes, and the solution temperature was then decreased to 60° C., and a light pink solid was deposited. After the deposited solid was collected by filtration under reduced pressure, the solid was washed with 400 mL of heptane at room temperature, and then washed with 800 mL of hot water four times. After washing, the light pink solid was dissolved in 600 mL of ethyl acetate, and 300 mL of toluene was then added to the obtained solution. When 800 mL of a 0.5% sodium hydroxide aqueous solution was added to the solution, followed by stirring, and the solution was left at rest. A water phase located on a lower side was changed to pink color and an organic phase located on an upper side was changed to solid color. The solution was separated, and the organic phase was collected. About 500 mL of a solvent was collected by distillation and concentrated. 800 mL heptane was added into a 2 L beaker. Furthermore, when a concentrated organic solvent solution was fed into the beaker, and stirring was continued for several minutes, a white crystal was deposited. The crystal was subjected to solid-liquid separation by filtration under reduced pressure, and washed with 800 mL of heptane. The crystal was dried at 90° C. in a drier for 9 hours, to obtain 94.7 g of AMTcOH (white solid). The structure of the AMTcOH was identified by NMR. The $^1$H-NMR spectrum is shown in FIG. 4.

$^1$H-NMR: (400 MHz, ACETONE-D6)

δ (ppm)=7.89 (2H, s), 7.15 (2H, d, J=2.2 Hz), 7.04 (2H, dd, J=8.0, 2.2 Hz), 6.74 (2H, d, J=8.0 Hz), 2.19 (6H, s), 1.79 (2H, s), 1.56-1.48 (8H, m), 1.21 (2H, s), 0.95 (6H, s)

<Synthesis of AMTcCN>

Next, 40 g (OH group equivalent: 188.3 g/eq., 0.21 mol in terms of hydroxy groups) of the AMTcOH obtained by the above described method and 21.5 g (0.21 mol, in an amount of 1.0 mol based on 1 mol of hydroxy group of the AMTcOH) of triethylamine were dissolved in 240 g of dichloromethane, and the obtained solution was defined as a solution 3.

The solution 3 was poured into a mixture of 22.2 g (0.36 mol, in an amount of 1.7 mol based on 1 mol of hydroxy group of the AMTcOH) of cyanogen chloride, 97.2 g of dichloromethane, 32.3 g (0.32 mol, in an amount of 1.5 mol based on 1 mol of hydroxy group of the AMTcOH) of 36% hydrochloric acid and 200 g of water under stirring, while keeping the solution temperature at −2 to −0.5° C. over 18 minutes. After completion of the pouring of the solution 3, the reaction solution was stirred at the same temperature as described above for 30 minutes, and a solution (solution 4) prepared by dissolving 21.5 g (0.21 mol, in an amount of 1.0 mol based on 1 mol of hydroxy group of the AMTcOH) of triethylamine in 21.5 g of dichloromethane was poured into the reaction solution over 1 minute. After completion of the pouring of the solution 4, the reaction solution was stirred at the same temperature as described above for 30 minutes, and the reaction was then terminated.

Thereafter, the reaction solution was left at rest, so that an organic phase was separated from a water phase. The obtained organic phase was washed with 130 g of 0.1 N hydrochloric acid, and then with 130 g of water five times. The electrical conductivity of the wastewater at the 5th water washing was 20 μS/cm, and it was confirmed that an ionic compound to be removed was sufficiently removed by washing with water.

Figure 5:
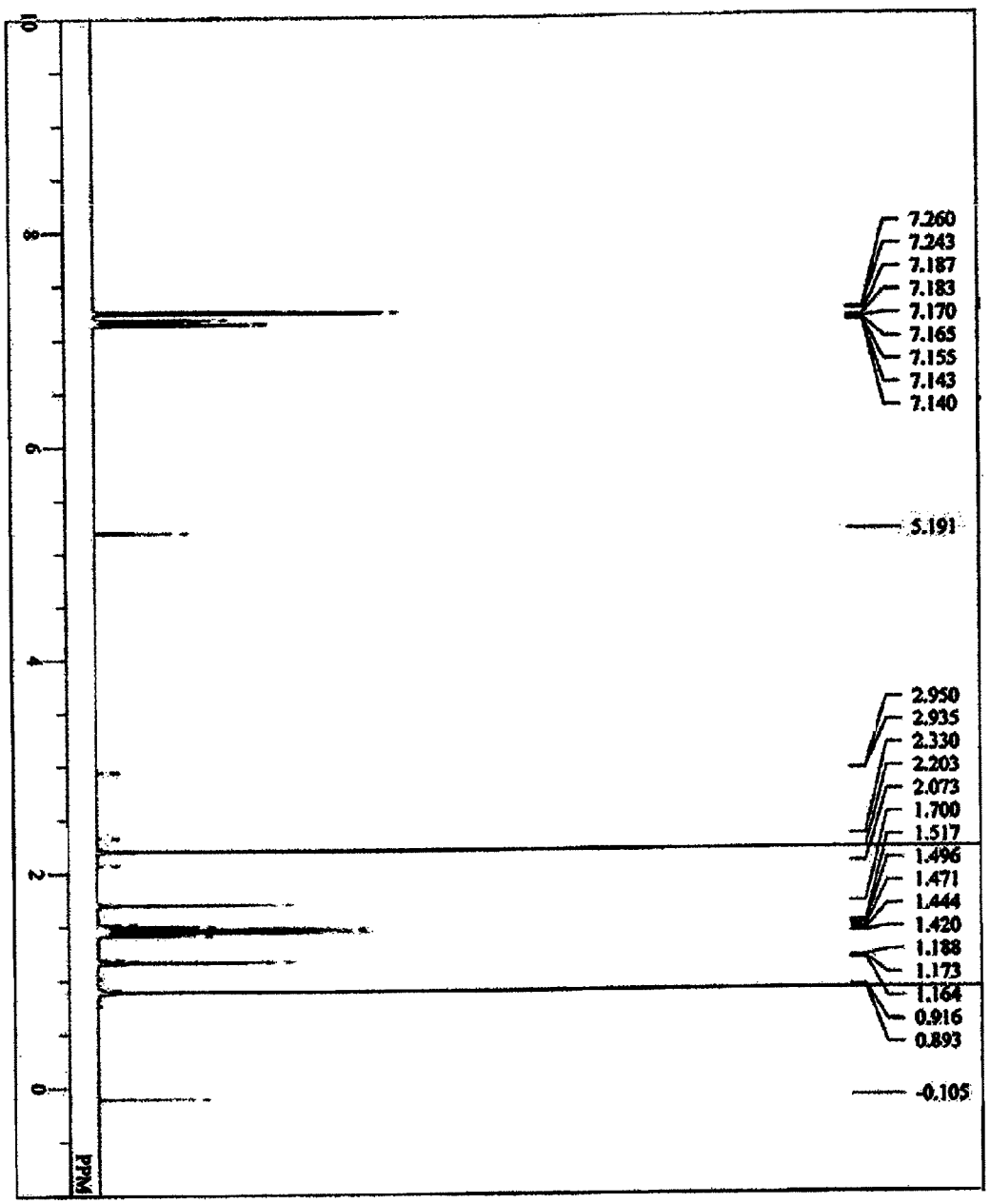
FIG. 5 is a $^1$H-NMR spectrum of a cyanate ester compound AMTcCN obtained in Example 2.

After completion of the water washing, the organic phase was concentrated under reduced pressure, and finally, it was concentrated and dried at 90° C. for 1 hour to obtain 46 g of the cyanate ester compound AMTcCN (white crystal) of interest. The structure of the obtained cyanate ester compound AMTcCN was identified by NMR. The $^1$H-NMR spectrum is shown in FIG. 5.

$^1$H-NMR: (500 MHz, CDCl3)

δ (ppm)=1.00 (s, 6H), 1.27 (s, 2H), 1.54 (d, J=12.5 Hz, 4H), 1.59 (d, J=12.5 Hz, 4H), 1.81 (s, 2H), 2.31 (s, 6H), 7.25 (d, J=2.0 Hz, 2H), 7.28 (dd, J=8.5, 2.0 Hz, 2H), 7.36 (d, J=8.5 Hz, 2H)

Figure 6:
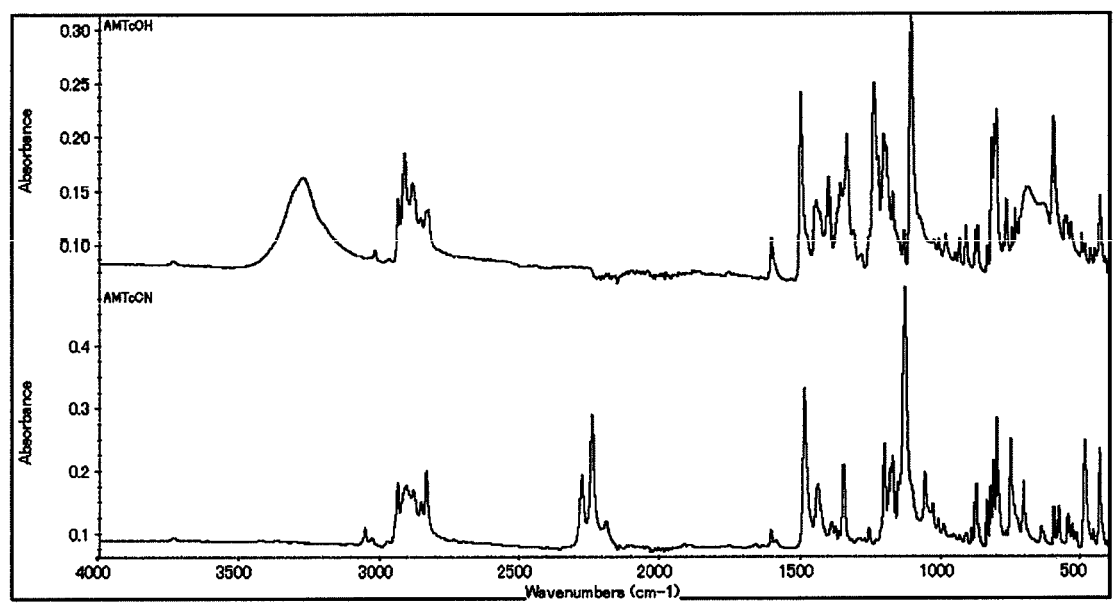
FIG. 6 is an FT-IR chart of a cyanate ester compound AMTcCN obtained in Example 2.

The IR spectrum of the AMTcCN exhibited absorptions of 2248 cm$^{-1}$ and 2284 cm$^{-1}$ (cyanate ester group) and did not exhibit the absorption of hydroxy group. The IR chart is shown in FIG. 6.

It was possible to dissolve 50% by mass or more of the AMTcCN in methyl ethyl ketone (MEK) at 25° C.

Example 3

Synthesis of 1,3-Bis(4-Cyanatophenyl)Adamantine (Hereinafter, Abbreviated as "uAMTCN")

uAMTCN represented by the following formula (9) was synthesized as described later.

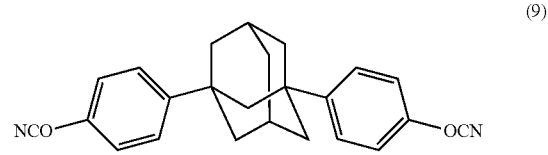

(9)

Synthesis of 1,3-Bis(4-Hydroxyphenyl)Adamantine (Hereinafter, Abbreviated as "uAMTOH")

First, uAMTOH represented by the following formula (10) was synthesized.

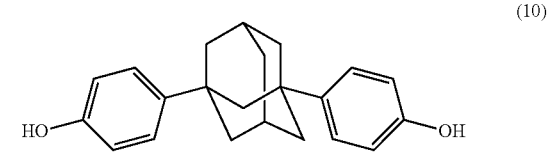 [SMILES: Oc1ccc(C23CC4CC(C2)CC(c2ccc(O)cc2)(C4)C3)cc1]

(10)

Figure 7:
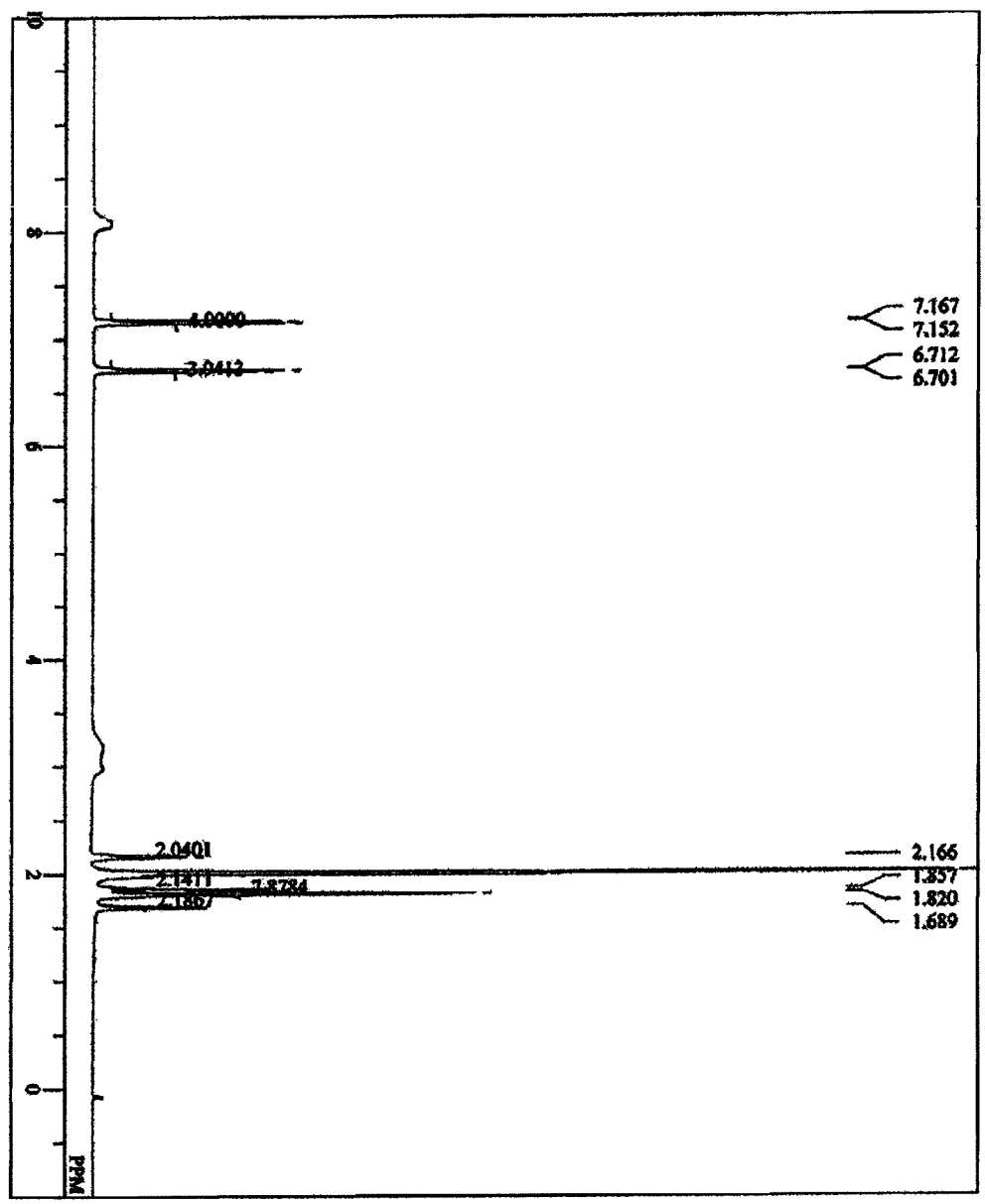
FIG. 7 is a $^1$H-NMR spectrum of a bisphenol compound uAMTOH obtained in Example 3.

Specifically, 70.6 g (0.42 mol) of adamantane-1,3-diol and 312.5 g (3.36 mol) of phenol were added into a reaction system under a nitrogen gas flow, and the obtained mixture was then melted by heating at 80° C. Then, while stirring, 40.62 g (0.42 mol) of methanesulfonic acid was added to the reaction mixture. The reaction was then carried out at 90° C. for 7 hours. Subsequently, 600 mL of water was added to the reaction solution, and the obtained mixture was stirred as it is for 1 hour. Thereafter, a precipitate was collected by filtration, and the obtained crystal was repeatedly washed with 600 mL of hot water three times. After washing, the crystal was dissolved in a mixed solvent of 1200 mL of ethyl acetate and 400 mL of toluene. The obtained solution was washed with 300 mL of a 0.5%-by-mass NaOH aqueous solution once, and thereafter, washing with 300 mL of water was repeatedly carried out until the pH of a water phase became neutral. After completion of the water washing, an organic phase was concentrated and dried under reduced pressure to obtain a solid. The obtained solid was dissolved in 600 mL of ethyl acetate at 65° C. To the obtained solution, 1200 mL of heptane was added at room temperature, and the obtained mixture was then stirred for 30 minutes to obtain a precipitate. The precipitate was collected by filtration, and it was then washed with 300 mL of heptane five times. Finally, the resultant was dried at 80° C. for 8 hours, to obtain 92 g of uAMTOH (white solid). The structure of the uAMTOH was identified by NMR. The $^1$H-NMR spectrum is shown in FIG. 7.

$^1$H-NMR: (500 MHz, ACETONE-D6)

δ (ppm)=1.69 (s, 2H), 1.82 (s, 8H), 1.86 (s, 2H), 2.17 (s, 2H), 6.71 (d, J=7.4 Hz, 4H), 7.16 (d, J=7.4 Hz, 4H)

<Synthesis of uAMTCN>

Next, 35 g (OH group equivalent: 160.2 g/eq., 0.218 mol in terms of hydroxy groups) of the uAMTOH obtained by the above described method and 22.5 g (0.218 mol, in an amount of 1.0 mol based on 1 mol of hydroxy group of the uAMTOH) of triethylamine were dissolved in 140 g of tetrahydrofuran, and the obtained solution was defined as a solution 5.

The solution 5 was poured into a mixture of 27.0 g (0.44 mol, in an amount of 2.0 mol based on 1 mol of hydroxy group of the uAMTOH) of cyanogen chloride, 63.0 g of dichloromethane, and 280 g of tetrahydrofuran under stirring, while keeping the solution temperature at −7 to −5° C. over 1 hour. After completion of the pouring of the solution 5, the reaction solution was stirred at the same temperature as described above for 30 minutes, and a solution (solution 6) prepared by dissolving 13.5 g (0.13 mol, in an amount of 0.6 mol based on 1 mol of hydroxy group of the uAMTOH) of triethylamine in 13.5 g of tetrahydrofuran was poured into the reaction solution over 15 minutes. After completion of the pouring of the solution 6, the reaction solution was stirred at the same temperature as described above for 30 minutes, and the reaction was then terminated.

Thereafter, triethyl ammonium chloride was collected by filtration, and the obtained filtrate was washed with 180 g of 0.1 N hydrochloric acid. The filtrate was then washed with 180 g of water seven times. The electrical conductivity of the wastewater at the 7th water washing was 20 μS/cm, and it was confirmed that an ionic compound to be removed was sufficiently removed by washing with water.

Figure 8:
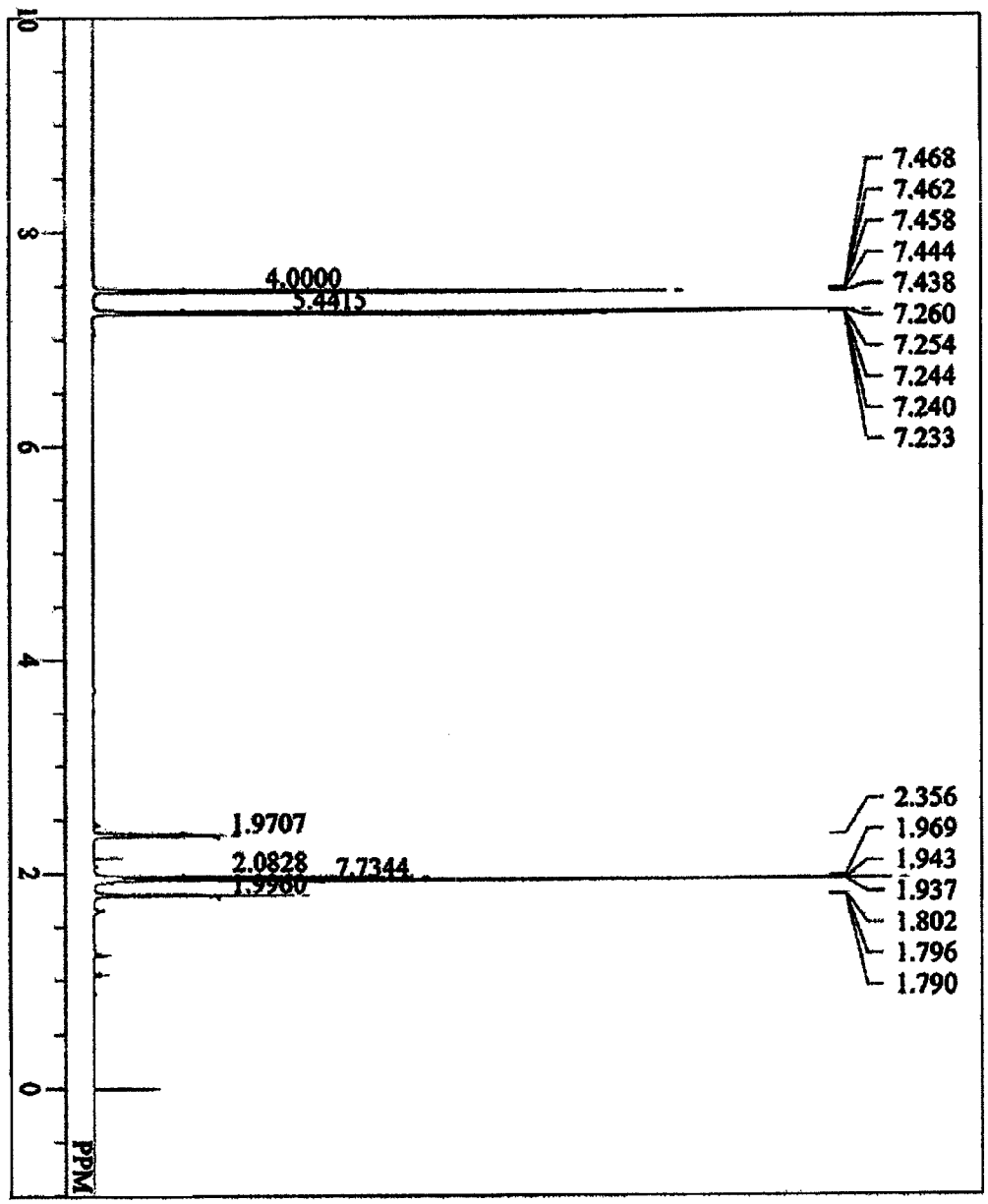
FIG. 8 is a $^1$H-NMR spectrum of a cyanate ester compound uAMTCN obtained in Example 3.

After washing, the organic phase was concentrated under reduced pressure, and it was concentrated and dried at 90° C. for 1 hour to obtain 39 g of a yellowish-white solid crystal. The obtained crystal was dissolved in 98 g of methyl ethyl ketone (MEK) and 21 g of n-hexane at 90° C., and then recrystallized. The obtained crystal was washed with 200 mL of n-hexane, and then dried under reduced pressure to obtain 20 g of the cyanate ester compound uAMTCN (light yellow crystal) of interest. The structure of the obtained cyanate ester compound uAMTCN was identified by NMR. The $^1$H-NMR spectrum is shown in FIG. 8.

$^1$H-NMR: (500 MHz, CDCl3)

δ (ppm)=1.79 (m, 2H), 1.94 (d, J=2.8 Hz, 8H), 1.97 (s, 2H), 2.36 (m, 2H), 7.25 (ddd, J=2.0, 3.2, 8.9 Hz), 7.45 (ddd, J=2.0, 3.2, 8.9 Hz)

Figure 9:
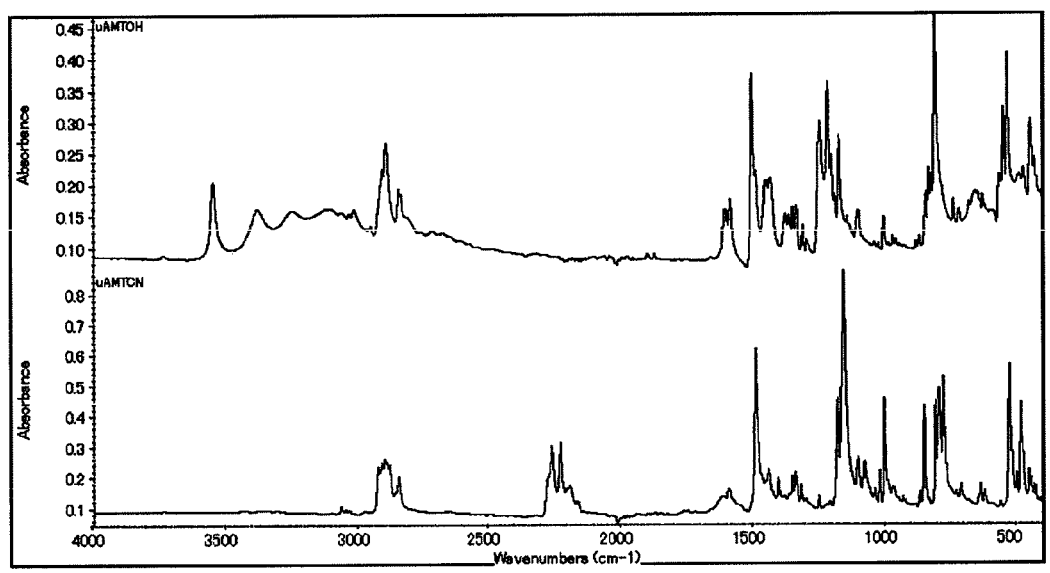
FIG. 9 is an FT-IR chart of a cyanate ester compound uAMTCN obtained in Example 3.

The IR spectrum of the uAMTCN exhibited absorptions of 2238 cm$^{-1}$ and 2266 cm$^{-1}$ (cyanate ester group) and did not exhibit the absorption of hydroxy group. The IR chart is shown in FIG. 9.

It was possible to dissolve 30% by mass or more of the uAMTCN in methyl ethyl ketone (MEK) at 25° C.

Example 4

<Preparation of Curable Resin Composition and Making of Hardened Product>

100 Parts by mass of the cyanate ester compound AMTCN obtained in Example 1 was placed in an eggplant-shaped flask, heated and melted at 150° C., and degassed by a vacuum pump. Then, 0.1 part by mass of zinc octylate (manufactured by Nihon Kagaku Sangyo Co., Ltd., trademark: "Nikka Octhix Zinc", metal content: 18%) was added, and the mixture was shaken and mixed for 1 minute to prepare a curable resin composition.

The obtained curable resin composition was injected into a mold made of an aluminum plate, a copper foil and a fluorine-coated stainless steel, and the mold was then placed in an oven, so that zinc octylate was uniformly dispersed in the resin composition at 150° C. Thereafter, the resulting composition was cured by vacuum pressing at 220° C. for 90 minutes at a rate of 20 kg/cm$^2$, thereby producing a hardened product with a 100-mm square and a thickness of 1.5 mm.

Example 5

A hardened product was obtained in the same manner as in Example 4 except that the resin composition was cured by vacuum pressing at 220° C. for 90 minutes at a rate of 20 kg/cm$^2$, and then heated at 220° C. for 6 hours.

Example 6

A hardened product was obtained in the same manner as in Example 4 except that 100 parts by mass of the AMTcCN obtained in Example 2 was used instead of 100 parts by mass of the AMTCN.

Example 7

A hardened product was obtained in the same manner as in Example 4 except that 100 parts by mass of the uAMTCN obtained in Example 3 was used instead of 100 parts by mass of the AMTCN.

Comparative Example 1

A hardened product was obtained in the same manner as in Example 4 except that 100 parts by mass of 2,2-bis(4-cyanatophenyl)propane (manufactured by Mitsubishi Gas Chemical Company, Inc., trade name: "skylex") was used instead of 100 parts by mass of the AMTCN, and zinc octylate was not added. It was possible to dissolve 50% by mass or more of 2,2-bis(4-cyanatophenyl)propane in methyl ethyl ketone at 25° C.

Comparative Example 2

A hardened product was obtained in the same manner as in Example 5 except that 100 parts by mass of 2,2-bis(4-cyanatophenyl)propane (manufactured by Mitsubishi Gas Chemical Company, Inc., trade name: "skylex") was used instead of 100 parts by mass of the AMTCN, and zinc octylate was not added.

Comparative Example 3

A hardened product was obtained in the same manner as in Example 4 except that 100 parts by mass of 2,2-bis(4-cyanatophenyl)propane (manufactured by Mitsubishi Gas Chemical Company, Inc., trade name: "skylex") was used instead of 100 parts by mass of the AMTCN, and the used amount of zinc octylate was changed to 0.05 part by mass from 0.1 part by mass.

Comparative Example 4

A hardened product was obtained in the same manner as in Example 5 except that 100 parts by mass of 2,2-bis(4-cyanatophenyl)propane (manufactured by Mitsubishi Gas Chemical Company, Inc., trade name: "skylex") was used instead of 100 parts by mass of the AMTCN, and the used amount of zinc octylate was changed to 0.05 part by mass from 0.1 part by mass.

Example 8

100 parts by mass of the AMTCN obtained in Example 1 was added into an eggplant-shaped flask, and it was then melted by heating at 150° C., followed by deaeration with a vacuum pump. Thereafter, the resultant was injected into a mold described in JIS-K 7238-2-2009, and the mold was then placed in an oven. Thereafter, the resulting composition was heated at 180° C. for 3 hours, and then heated at 250° C. for 3 hours for curing, thereby producing a hardened product with a 100-mm square and a thickness of 1.5 mm.

Example 9

A hardened product was obtained in the same manner as in Example 8 except that 100 parts by mass of the AMTcCN obtained in Example 2 was used instead of 100 parts by mass of the AMTCN.

Example 10

A hardened product was obtained in the same manner as in Example 8 except that 100 parts by mass of the uAMTCN obtained in Example 3 was used instead of 100 parts by mass of the AMTCN.

Comparative Example 5

A hardened product was obtained in the same manner as in Example 8 except that 100 parts by mass of 2,2-bis(4-cyanatophenyl)propane (manufactured by Mitsubishi Gas Chemical Company, Inc., trade name: "skylex") was used instead of 100 parts by mass of the AMTCN.

The properties of individual hardened products obtained as described above were evaluated by the following method.

(Glass Transition Temperature (Tg))

In accordance with JIS-K7244-3 (JIS C6481), in each of Examples 4 and 5 and Comparative Examples 1 to 4, a dynamic viscoelasticity of a hardened product was measured using a dynamic viscoelasticity measurement device (manufactured by TA Instruments Japan, model "Q800"), at an initiation temperature of 30° C., at a termination temperature of 400° C., at a temperature increase rate of 10° C./min, and at a measurement frequency of 10 Hz. In each of Examples 6 to 8 and Comparative Example 5, a dynamic viscoelasticity of a hardened product was measured using a dynamic viscoelasticity measurement device (manufactured by TA Instruments Japan, model "AR2000"), at an initiation temperature of 30° C., at a termination temperature of 400° C., at a temperature increase rate of 3° C./min, and at a measurement frequency of 1 Hz. A maximum value of a loss elastic modulus (E") obtained upon the measurement was defined as a glass transition temperature. The glass transition temperature is an index of heat resistance.

(Coefficiency of Thermal Expansion)

In accordance with JIS-K-7197-2012 (JIS C6481), thermo-mechanical analysis was carried out in an expansion/compression mode, employing a thermomechanical analysis apparatus (manufactured by SII NanoTechnology Inc., trade name: TMA/SS6100), using a hardened product test piece of 5 mm×5 mm×1.5 mm, at an initiation temperature of 30° C., at a termination temperature of 330° C., at a temperature increase rate of 10° C./min, and at a load of 0.05 N (49 mN). The average amount of thermal expansion per ° C. was measured in a range of 60 to 120° C.

(Flame Retardancy)

A flame retardancy test was carried out in accordance with UL94. The size of a hardened product test piece was set to 100 mm×20 mm×1.5 mm.

(Weight Reduction Rate (%))

In accordance with JIS-K7120-1987, a weight was measured employing a thermal gravimetric-differential thermal analyzer (manufactured by SII NanoTechnology Inc., trade name: TG/DTA6200), using a hardened product test piece of 3 mm×3 mm×1.5 mm, at an initiation temperature of 30° C., at a termination temperature of 550° C., at a temperature increase rate of 10° C./min, and in a nitrogen atmosphere. A weight reduction rate at 500° C. was calculated according to the following formula.

$$\text{Weight Reduction Rate (\%)} = (D-E)/D \times 100$$

Herein, D represents the weight at the initiation temperature, and E represents the weight at 500° C. In addition to the evaluation of the flame retardancy, a large amount of residue upon thermal decomposition, namely, a low weight reduction rate is also evaluated as flame retardancy.

The evaluation results are shown in Tables 1 and 2.

As is apparent from Tables 1 and 2, it was confirmed that a bifunctional cyanatophenyl-based cyanate ester compound having an adamantane skeleton of the present invention has the excellent solvent solubility, and also has excellent handling properties. It was confirmed that the hardened product of the curable resin composition containing the cyanate ester compound of the present invention has a lower coefficient of thermal expansion and more excellent flame retardancy and heat resistance than those of a hardened product containing a conventional cyanate ester compound.

TABLE 1

|  |  |  | Example 4 | Example 5 | Example 6 | Example 7 |
|---|---|---|---|---|---|---|
| Composition | AMTCN | Part by mass | 100 | 100 | 0 | 0 |
|  | AMTcCN |  | 0 | 0 | 100 | 100 |
|  | 2,2-bis(4-cyanatophenyl)propane |  | 0 | 0 | 0 | 0 |
|  | Zinc octylate |  | 0.1 | 0.1 | 0.1 | 0.1 |
| Curing condition | Vacuum pressing | 220° C., 90 minutes | Presence | Presence | Presence | Presence |
|  | Heating | 220° C., 6 hours | Absence | Presence | Absence | Presence |

TABLE 1-continued

|  |  |  |  |  |  |  |
|---|---|---|---|---|---|---|
| Physical property of monomer | MEK solubility | % by mass | >50 | >50 | >50 | >50 |
| Physical properties of hardened product | Tg | °C. | 323 | >400 | 318 | 335 |
|  | Coefficiency of thermal expansion | ppm/°C. | 51 | 49 | 58 | 58 |
|  | UL94 | Determination | V-0 | V-0 | Non-measurement | Non-measurement |
|  | Weight reduction rate | % | 10 | 13 | 16 | 17 |

|  |  |  | Comparative Example 1 | Comparative Example 2 | Comparative Example 3 | Comparative Example 4 |
|---|---|---|---|---|---|---|
| Composition | AMTCN | Part by mass | 0 | 0 | 0 | 0 |
|  | AMTcCN |  | 0 | 0 | 0 | 0 |
|  | 2,2-bis(4-cyanatophenyl)propane |  | 100 | 100 | 100 | 100 |
|  | Zinc octylate |  | 0 | 0 | 0.05 | 0.05 |
| Curing condition | Vacuum pressing | 220° C., 90 minutes | Presence | Presence | Presence | Presence |
|  | Heating | 220° C., 6 hours | Absence | Presence | Absence | Presence |
| Physical property of monomer | MEK solubility | % by mass | >50 | >50 | >50 | >50 |
| Physical properties of hardened product | Tg | °C. | 196 | 307 | 298 | 311 |
|  | Coefficiency of thermal expansion | ppm/°C. | 59 | 53 | 56 | 50 |
|  | UL94 | Determination | Completely burned | Completely burned | Completely burned | Completely burned |
|  | Weight reduction rate | % | 41 | 41 | 40 | 41 |

TABLE 2

|  |  |  | Example 8 | Example 9 | Example 10 | Comparative Example 5 |
|---|---|---|---|---|---|---|
| Composition | AMTCN | Part by mass | 100 | 0 | 0 | 0 |
|  | AMTcCN |  | 0 | 100 | 0 | 0 |
|  | uAMTCN |  | 0 | 0 | 100 | 0 |
|  | 2,2-bis(4-cyanatophenyl)propane |  | 0 | 0 | 0 | 100 |
|  | Zinc octylate |  | 0 | 0 | 0 | 0 |
| Physical property of monomer | MEK solubility | % by mass | >50 | >50 | >30 | >50 |
| Physical properties of hardened product | Tg | °C. | 353 | 306 | 342 | 312 |
|  | Coefficiency of thermal expansion | ppm/°C. | 37 | 38 | 42 | 48 |
|  | UL94 | Determination | V-0 | V-0 | V-0 | Completely burned |
|  | Weight reduction rate | % | 21 | 30 | 32 | 44 |

Example 11

50 parts by mass of the AMTCN obtained as described above, 50 parts by mass of a biphenyl aralkyl-based epoxy resin (product name: "NC-3000-FH", manufactured by Nippon Kayaku Co., Ltd.), 100 parts by mass of fusion silica (product name: "SC2050 MB", manufactured by Admatechs), and 0.05 part by mass of zinc octylate (manufactured by Nihon Kagaku Sangyo Co., Ltd.) were mixed to obtain a varnish. This varnish was diluted with methyl ethyl ketone, and an E-glass woven fabric having a thickness of 0.1 mm was then impregnated and coated with this varnish. The resulting product was dried by heating at 150° C. for 5 minutes, to obtain a prepreg containing 50 parts by mass of a resin solid content based on 100 parts by mass of the total amount of the resin solid content and fusion silica.

The obtained eight prepregs were laminated on one another, and electrolytic copper foils (trade name: "JDLCN", manufactured by JX Nippon Mining & Metals Corporation) each having a thickness of 12 μm were disposed on both sides in a lamination direction of the obtained prepreg product. The obtained product was subjected to lamination molding at a pressure of 30 kg f/cm², at a temperature of 220° C. for 120 minutes, to obtain a metal foil clad laminate in which the thickness of an insulating layer was 0.8 mm. Using the obtained metal foil clad laminate, a water absorption rate and heat resistance after moisture absorption were evaluated. The results are shown in Table 3.

(Measurement Methods and Evaluation Methods)
1) Water Absorption Rate

In accordance with JIS C6480, a sample with a size of 30 mm×30 mm was treated using a pressure cooker tester (manufactured by Hirayama Manufacturing Corp., model: PC-3) at 121° C. at a pressure of 2 atm for 1, 3, and 5 hours. Thereafter, a water absorption rate was measured.

2) Heat Resistance After Moisture Absorption

A test piece prepared by removing the entire copper foil, other than a half of one surface of a sample of 50 mm×50 mm, by etching was treated using a pressure cooker tester (manufactured by Hirayama Manufacturing Corp., model: PC-3) at 121° C. at a pressure of 2 atm for 3, 4 and 5 hours. Thereafter, the test piece was immersed in a solder at 260° C. for 60 seconds. Thereafter, a change in the appearance was observed by visual inspection. The results shown in Table 3 are (the number of test pieces having blisters occurred/the number of test pieces provided for tests).

Comparative Example 6

A metal foil clad laminate in which the thickness of an insulating layer was 0.8 mm was obtained in the same manner as in Example 11 except that 50 parts by mass of a bisphenol A-based cyanate ester compound (product name: "CA210" manufactured by Mitsubishi Gas Chemical Company, Inc.) was used instead of 50 parts by mass of the AMTCN, and the used amount of zinc octylate was changed to 0.03 part by mass from 0.05 part by mass. The evaluation results of the obtained metal foil clad laminate are shown in Table 3.

Comparative Example 7

A metal foil clad laminate in which the thickness of an insulating layer was 0.8 mm was obtained in the same manner as in Example 11 except that 50 parts by mass of a phenol novolac-based cyanate ester compound (product name: "Primaset PT-30" manufactured by Lonza Japan) was used instead of 50 parts by mass of the AMTCN; the used amount of zinc octylate was changed to 0.04 part by mass from 0.05 part by mass; and a temperature and a time during drying after impregnating and coating were respectively changed to 165° C. and 4 minutes from 150° C. and 5 minutes. The evaluation results of the obtained metal foil clad laminate are shown in Table 3.

TABLE 3

| | | Example 11 | Comparative Example 6 | Comparative Example 7 |
|---|---|---|---|---|
| Water absorption rate (%) | After processing for 5 hours | 0.39 | 0.38 | 0.52 |
| Heat resistance after moisture absorption | After processing for 5 hours | 0/4 | 3/4 | 1/4 |

As is apparent from Table 3, it was confirmed that a prepreg and a printed wiring board or the like which have not only low water-absorbing property but also excellent heat resistance after moisture absorption can be realized with the use of the curable resin composition for printed wiring boards of the present invention.

The present application is based on a Japanese patent application filed with the Japan Patent Office on Oct. 25, 2013 (Japanese Patent Application No. 2013-222021) and a Japanese patent application filed with the Japan Patent Office on Jan. 23, 2014 (Japanese Patent Application No. 2014-010135); and the disclosure of which is hereby incorporated by reference.

INDUSTRIAL APPLICABILITY

The cyanate ester compound of the present invention has excellent solvent solubility and provides a hardened product having a low coefficient of thermal expansion, and excellent flame retardancy and heat resistance. Therefore, the present invention is extremely useful as a highly functional polymer material, and has industrial applicability for electrical insulating materials, semiconductor sealing materials, adhesives for electronic parts, lamination materials, resists, and buildup laminate materials, as well as fixing materials, structural members, reinforcing agents, and casting materials, or the like in the fields of civil engineering and construction, electrics and electronics, automobiles, railroads, ships, aircraft, sporting goods, arts and crafts or the like as a material having excellent thermal, electrical, and mechanical properties. The resin composition of the present invention can be widely and effectively used, for example, as an electrical insulating material, a semiconductor plastic package, a sealing material, an adhesive, a laminating material, a resist, and a build-up laminating material or the like for various intended uses such as electrical and electronic materials, machine tool materials, and aviation materials. In particular, the present resin composition can be particularly effectively used as a material for printed wiring boards which is applicable to high integration and densification of recent information terminal devices or communication devices or the like. The laminate and metal foil clad laminate of the present invention, or the like have not only low water-absorbing property but also excellent heat resistance after moisture absorption. Accordingly, the industrial practicability of the resin composition is extremely high.

The invention claimed is:

1. A cyanate ester compound represented by the following formula (1):

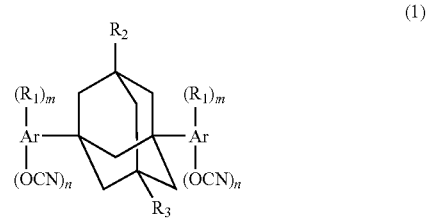

wherein Ar represents an aromatic ring; $R_1$ each independently represents a hydrogen atom, an alkyl group, or an aryl group; n each independently represents an integer of 1 to 3; m+n is the same as the total number of hydrogen atoms in a monovalent aromatic group comprising the aromatic ring and the hydrogen atoms; $R_2$ represents a hydrogen atom (excluding a case where Ar represents a benzene ring; n each represents 1; $R_1$ represents a hydrogen atom; m each represents 4, and a cyanate group is bonded to the benzene ring in the 4-position relative to an adamantyl group), or an alkyl group having 1 to 4 carbon atoms; and $R_3$ represents a hydrogen atom or an alkyl group having 1 to 4 carbon atoms.

2. The cyanate ester compound according to claim 1, wherein, in the formula (1), Ar represents a benzene ring; n represents 1; and $R_2$ represents a methyl group, an ethyl group, a propyl group, an isopropyl group, or a t-butyl group.

3. The cyanate ester compound according to claim 1, wherein Ar represents a benzene ring; and n represents 2 or 3.

4. The cyanate ester compound according to claim 1, wherein Ar represents an aromatic ring other than a benzene ring.

5. A curable resin composition comprising a cyanate ester compound represented by the following formula (1):

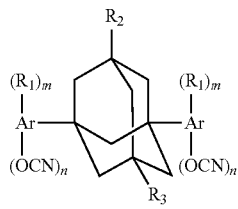

(1)

wherein Ar represents an aromatic ring; $R_1$ each independently represents a hydrogen atom, an alkyl group, or an aryl group; n represents an integer of 1 to 3; m+n represents an integer representing the total number of monovalent atoms and groups bonded to Ar; $R_2$ represents a hydrogen atom or an alkyl group having 1 to 4 carbon atoms; and $R_3$ represents a hydrogen atom or an alkyl group having 1 to 4 carbon atoms.

6. The curable resin composition according to claim 5, further comprising one or more selected from the group consisting of a cyanate ester compound other than the cyanate ester compound represented by the formula (1), an epoxy resin, an oxetane resin, and a compound having a polymerizable unsaturated group.

7. The curable resin composition according to claim 5, wherein, in the cyanate ester compound represented by the formula (1), Ar represents a benzene ring; n represents 1; and $R_2$ represents a methyl group, an ethyl group, a propyl group, an isopropyl group, or a t-butyl group.

8. The curable resin composition according to claim 5, wherein, in the cyanate ester compound represented by the formula (1), Ar represents a benzene ring, and n represents 2 or 3.

9. The curable resin composition according to claim 5, wherein, in the cyanate ester compound represented by the formula (1), Ar represents an aromatic ring other than a benzene ring.

10. A hardened product obtained by curing the curable resin composition according to claim 5.

11. A prepreg for structural materials comprising a base material and the curable resin composition according to claim 5 with which the base material is impregnated or coated.

12. A sealing material comprising the curable resin composition according to claim 5.

13. A fiber-reinforced composite material comprising the curable resin composition according to claim 5.

14. An adhesive comprising the curable resin composition according to claim 5.

15. The curable resin composition according to claim 5, further comprising an epoxy resin.

16. The curable resin composition according to claim 15, wherein a content of the cyanate ester compound represented by the formula (1) is 1 to 90 parts by mass based on 100 parts by mass of a resin solid content in the curable resin composition.

17. The curable resin composition according to claim 15, further comprising an inorganic filler.

18. The curable resin composition according to claim 17, wherein a content of the inorganic filler is 50 to 1600 parts by mass based on 100 parts by mass of a resin solid content in the curable resin composition.

19. The curable resin composition according to claim 15, further comprising one or more selected from the group consisting of a maleimide compound, a phenolic resin, and a cyanate ester compound other than the cyanate ester compound represented by the formula (1).

20. The curable resin composition according to claim 15, wherein the epoxy resin is one or more selected from the group consisting of a biphenyl aralkyl-based epoxy resin, a naphthylene ether-based epoxy resin, a multifunctional phenol-based epoxy resin, and a naphthalene-based epoxy resin.

21. A metal foil clad laminate comprising one or more of the prepreg according to claim 11 and a metallic foil disposed on one or both surfaces of the prepreg.

22. A laminate comprising a support and a resin layer formed on a surface of the support by coating and drying of the curable resin composition according to claim 5.

23. A printed wiring board comprising an insulating layer and a conductor layer formed on a surface of the insulating layer, wherein the insulating layer comprises the curable resin composition according to claim 5.

* * * * *